US009353164B2

(12) United States Patent
Chuah et al.

(10) Patent No.: US 9,353,164 B2
(45) Date of Patent: May 31, 2016

(54) CARDIAC-SPECIFIC NUCLEIC ACID REGULATORY ELEMENTS AND METHODS AND USE THEREOF

(75) Inventors: Lay Khim Chuah, Lovenjoel (BE); Thierry Vandendriessche, Lovenjoel (BE); Pieter De Bleser, Buggenhout (BE)

(73) Assignees: VIB VZW, Ghent (BE); Life Sciences Research Partners VZW, Leuven (BE); Universiteit Gent, Ghent (BE)

( * ) Notice: Subject to any disclaimer, the term of this patent is extended or adjusted under 35 U.S.C. 154(b) by 0 days.

(21) Appl. No.: 13/504,614

(22) PCT Filed: Oct. 29, 2010

(86) PCT No.: PCT/EP2010/066474
§ 371 (c)(1),
(2), (4) Date: Jun. 19, 2012

(87) PCT Pub. No.: WO2011/051450
PCT Pub. Date: May 5, 2011

(65) Prior Publication Data
US 2012/0252882 A1  Oct. 4, 2012

(30) Foreign Application Priority Data

Oct. 29, 2009  (EP) .................................... 09174519

(51) Int. Cl.
| | |
|---|---|
| C12N 15/113 | (2010.01) |
| C12N 15/85 | (2006.01) |
| C07K 14/47 | (2006.01) |
| C07K 14/805 | (2006.01) |
| A61K 48/00 | (2006.01) |

(52) U.S. Cl.
CPC ......... *C07K 14/4702* (2013.01); *C07K 14/4716* (2013.01); *C07K 14/805* (2013.01); *C12N 15/85* (2013.01); *A61K 48/00* (2013.01); *C12N 2799/025* (2013.01); *C12N 2830/008* (2013.01); *C12N 2830/15* (2013.01); *C12N 2830/30* (2013.01); *C12N 2830/42* (2013.01); *C12N 2830/85* (2013.01)

(58) Field of Classification Search
CPC ... A61K 38/2242; A61K 38/18; A61K 48/00; A61K 9/0019; C12N 5/0657; C12N 2830/42; C12N 2830/008; C12N 2830/30; C12N 2830/15; C12N 15/85; C12N 2799/025; C12N 2830/85; C07K 14/4702; C07K 14/805; C07K 14/4716
See application file for complete search history.

(56) References Cited

U.S. PATENT DOCUMENTS

| 2008/0193941 A1* | 8/2008 | Cohen et al. ...................... 435/6 |
| 2010/0190840 A1 | 7/2010 | Koch et al. |
| 2011/0027234 A1* | 2/2011 | Gepstein et al. ............. 424/93.7 |
| 2011/0097761 A1* | 4/2011 | Chamberlain et al. ....... 435/91.1 |

FOREIGN PATENT DOCUMENTS

| WO | 0111064 A2 | 2/2001 |
| WO | 0151006 A2 | 7/2001 |
| WO | 2008054713 A2 | 5/2008 |
| WO | 2008126083 A2 | 10/2008 |
| WO | 2009130208 A2 | 10/2009 |
| WO | 2011051450 A1 | 5/2011 |

OTHER PUBLICATIONS

Su et al. Adeno-associated viral vector-mediated vascular endothelial growth factor gene transfer induces neovascular formation in ischemic heart PNAS Dec. 5, 2000 vol. 97 No. 25 13801-13806.*
Duan et al. Gene Regulation: Regulated Systems and Cell Engineering Development of a Novel Gene Regulation System Downstream of Promoter Molecular Therapy May 2005 vol. 11, Supplement 1.*
Pacak et al. Recombinant Adeno-Associated Virus Serotype 9 Leads to Preferential Cardiac Transduction In Vivo Circ Res. 2006;99:e3-e9; doi: 10.1161/01.RES.0000237661.18885.f6.*
Mulller et al. "Targeting the heart with gene therapy-optimized gene delivery methods." Cardiovascular Research (2007); 73: pp. 453-462.*
Vinge et al. "Gene Therapy in Heart Failure." Circ Res. (2008);102: pp. 1458-1470.*
Bestor, Thomas "Gene silencing as a threat to the success of gene therapy." The Journal of Clinical Investigation (2000);105(4): pp. 409-411.*
Lyon et al., Gene Therapy: Targeting the Myocardium, Heart, Jan. 1, 2008, pp. 89-99, vol. 94, No. 1, BMJ, London, GB.
Lemonnier et al., Characterization of a Cardiac-Specific Enhancer, Which Directs Alpha-Cardiac Actin Gene Transcription in the Mouse Adult Heart, Journal of Biological Chemistry, Dec. 31, 2004, pp. 55651-55658, vol. 279, No. 53, American Society for Biochemistry and Molecular Biology, Inc. US.
Geohringer et al., Prevention of Cardiomyopathy in Delta-Sarcoglycan Knockout Mice After Systemic Transfer of Targeted Adeno-Associated Viral Vectors, Cardiovascular Research, Jun. 2009, pp. 404-410, vol. 82, No. 3.
Pacak et al., Tissue Specific Promoters Improve Specificity of AAV9 mediated Transgene Expression Following Intra-Vascular Gene Delivery in Neonatal Mice, Genetic Vaccines and Therapy, Sep. 23, 2008, p. 13, Biomed Central, London, GB.

(Continued)

*Primary Examiner* — Thaian N Ton
*Assistant Examiner* — Titilayo Moloye
(74) *Attorney, Agent, or Firm* — TraskBritt, P.C.

(57) ABSTRACT

The present invention relates to nucleic acid regulatory elements that are able to enhance cardiac-specific expression of genes, methods employing these regulatory elements and uses of these elements. Expression cassettes and vectors containing these nucleic acid regulatory elements are also disclosed. The present invention is particularly useful for applications using gene therapy.

21 Claims, 8 Drawing Sheets

(56) References Cited

OTHER PUBLICATIONS

Vandendriessche et al., Efficacy and Safety of Adeno-Associaed Viral Vectors Based on Serotype 8 and 9 vs. Lentiviral Vectors for Hemophilia B Gene Therapy, Journal of Thrombosis and Haemostasis, Jan. 2007, pp. 16-24, vol. 5, No. 1.

PCT International Search Report, PCT/EP2010/066474, dated Feb. 2, 2011.

Database Geneseq [Online], Aug. 26, 2004, Human soft tissue sarcoma-upregulated DNA, SEQ ID 740, Database Accession No. ADQ17923.

Database EMBL [Online], Aug. 26, 1996, Human fetal heart, Lambda ZAP Express *Homo sapiens* cDNA 5', mRNA sequence, Database Accession No. AA090235.

Database Geneseq [Online], Dec. 24, 2008, Human myosin light chain-2v (MLC-2v) promoter sequence, SEQ ID 2, Database Accession No. ATS14125.

Database EMBL [Online], Jul. 6, 1989, *Homo sapiens* MLC-1V/Sb isoform gene, exon 1, Database Accession No. M24242.

* cited by examiner

Fig. 1

```
         -370        -360        -350        -340        -330        -320
          |           |           |           |           |           |
Mouse:   GGTGACCCTT  ACCCAGTTGT  TCAACTCACC  CTTCAGATTA  AAAATAACTG  AGGTAAGGGC
Rat:     ACCCTTACCC  AGTGTGTTCA  ACTCAGCCTT  TCAGATTAAA  AATAACTAAG  GTAAGGGCCA
Human:   GTGACCCTCA  CCCATGTTTT  CAGTCTCACT  TCGGGGGAAA  AATAACTGAG  GTAAGGGCCA
                                                          MEF2

-310        -300        -290        -280        -270        -260
          |           |           |           |           |           |
Mouse:   CTGGGTAGGG  GAGGTGGTGT  GAGACGCTCC  TGTCTCTCCT  CTATCTGCCC  ATCGGCCCTT
Rat:     TGTGGGTAGG  GGAGGTGGTG  TGAGACGGTC  CTGTCTCTCC  TCTATCTGCC  CATCGGCCCT
Human:   TGGCAGGGTG  GGAGAGGCGG  TGTGAGAAGG  TCCAGTCTTC  CCAGCTATCT  GCTCATCAGC
                                             [3`CAAAGGGC  CGATGGGCAG  ATAGAGGAGA 5`]
                                                           GATA       GATA
                                                              PRE-D -250        -240        -230        -220        -210        -200
          |           |           |           |           |           |
Mouse:   TGGGGAGGAG  GAATGTGCCC  AAGGACTAAA  AAAAGGCCAT  GGAGCCAGAG  GGGCGAGGGC
Rat:     TTGGGGAGGA  GGAAATGTGC  CCAAGGACTA  AAAAAGGCCT  GGAGCCAGAG  GGGCTAGGGC
Human:   CCTTTGAAGG  GGAGGAATCT  GCCCAAGGAC  TAAAAAAAGG  CCGTGGAGCC  AGAGAGGCTG
                   M-CAT                    A/T-rich -190        -180        -170        -160        -150        -140
          |           |           |           |           |           |
Mouse:   AACAGACCTT  TCATGGGCAA  ACCTTGGGGC  CCTCCTGTCC  TCCTGTCACC  TCCAGAGCCA
Rat:     TAAGCAGACC  TTTCATGGGC  AAACCTCAGG  GCTGCTGTCC  TCCTGTCACC  TCCAGAGCCA
Human:   GGGCAGCAGA  CCTTTCAAGG  GCAAATCAGG  GGCCCTGCTG  TCCTCCTGTC  ACCTCCAGAG
                  CArG1                                              TEF (TRE1)

-130        -120        -110        -100        -90         -80
          |           |           |           |           |           |
Mouse:   AGGGATCAAA  GGAGGAGGAG  CCAGGACAGG  AGGGAAGTGG  GAGGGAGGGT  CCCAGCAGAG
Rat:     AGGGATCAAA  GGAGGAGGAG  CCAGACAGGA  GGGATGGGAG  GGAGGCTCCC  AGCAGATGAC
Human:   CCAAAGGATC  AAAGGAGGAC  CACCCAGCAG  GGGAGAGAGG  TGGGAGGGAG  GGTTCCTGTC -70         -60         -50         -40         -30         -20
          |           |           |           |           |           |
Mouse:   GACTCCAAAT  TTAGGCAGCA  GGCATATGGG  ATGGGATATA  AAGGGGCTGG  AGCACTGAGA
Rat:     TCCAAATTTA  GGCAGCAGGC  ACGTGGAATG  AGCTATAAAG  GGGCTGGAGC  CCTCACAGCT
Human:   ACCTCCAGAG  CCTCCGGAAG  GACTCCAAAT  TTAGACAGAG  GGTGGGGAA   ACGGGATATA
              CArG2 (mouse)
              A/T-rich(rat)      E-box/M-CAT(rat)

-10
          |
Mouse:   GCTGTCAGAGA  (SEQ ID NO: 17)
Rat:     GTCAGACCGAG  (SEQ ID NO: 18)
Human:   AAGGAACTGGA  (SEQ ID NO: 19)
```

CARDIAC-SPECIFIC NUCLEIC ACID REGULATORY ELEMENTS AND METHODS AND USE THEREOF

CROSS-REFERENCE TO RELATED APPLICATIONS

This application is a national phase entry under 35 U.S.C. §371 of International Patent Application PCT/EP2010/066474, filed Oct. 29, 2010, designating the United States of America and published in English as International Patent Publication WO2011/051450 A1 on May 5, 2011, which claims the benefit under Article 8 of the Patent Cooperation Treaty to United Kingdom Application Serial No. 09174519.0, filed Oct. 29, 2009.

TECHNICAL FIELD

The disclosure relates to biotechnology and nucleic acid regulatory elements that are able to enhance cardiac-specific expression of genes, methods employing these regulatory elements and uses of these elements. Expression cassettes and vectors containing these nucleic acid regulatory elements are also disclosed. The disclosure is particularly useful for applications using gene therapy.

BACKGROUND

Heart related problems remain a major public-health issue with high prevalence, poor clinical outcomes, and large health-care costs (Krum et al., 2009). +The major and ultimate result, heart failure, leads to significant morbidity and mortality. The primary causes of most syndromes contributing to heart failure include mainly hypertension, coronary artery disease, cardiomyopathy, infiltrative syndromes or inflammation results in a myocardium with a mixture of replacement fibrosis and diabetes. Though these conditions are treatable, they do not constitute a cure and only slow down the progression of the disease, which ultimately results in fatal heart failure (LaPointe et al., 2002). In recent times, the molecular pathways involved in induction and progression of most common cardiac diseases have been elucidated through advances in molecular cardiology and have led to the identification of numerous causative genes and proteins associated with these diseases. Gene therapy shows a promising means to control the production of such proteins to prevent and treat cardiac diseases (Lyon et al., 2008).

Gene therapy provides a possible alternative strategy to treat myocardial dysfunction (Fomicheva et al., 2008) whereby a therapeutic gene is delivered to the heart and expressed at high enough levels over a prescribed period of time to effect a therapeutic response (LaPointe et al., 2002). Among the heart-related conditions being targeted by gene therapy are genetic cardiomyopathies like Duchenne muscular dystrophy (DMD) (Bostick et al., 2009), hypertrophic cardiomyopathy (Jacques et al., 2008), and diabetic cardiomyopathy (Wang et al., 2009). Over the past decade, gene therapy has shown promising results in preclinical studies in animal models to treat heart failure including arrhythmia, restenosis (Müller et al., 2007), ischaemia and hypoxia (Fomicheva et al., 2008). For instance, therapeutic angiogenesis has been explored by gene therapy to treat cardiac ischemia by over-expressing genes encoding angiogenic factors (e.g., vascular endothelial growth factor or VEGF (Müller et al., 2007; Stewart et al., 2009). In addition, gene therapy provides a potential strategy to create an immune privileged site within the transplanted heart to prevent immune rejection in transplant patients (Vassalli et al., 2009). Clinical successes of gene therapy to treat cardiac diseases have been slower than originally predicted, due to challenges inherent to gene transfer efficacy: inadequate delivery to the target tissue, loss of therapeutic effect, and dose-limiting interactions with the host immune system (Sasano et al., 2007). Delivery issues are the most challenging among these. Reported methods of myocardial delivery include intramyocardial injection, coronary catheterization, pericardial delivery, ventricular cavity infusion during aortic cross-clamping, and perfusion during cardiopulmonary bypass (Müller et al., 2007; Sasano et al., 2007).

The use of plasmid/naked DNA has been demonstrated to yield therapeutic effects in animal models and patients with intractable myocardial ischemia. But since naked DNA cannot enter cells spontaneously with sufficient efficiency, systemic injection of naked DNA is an inefficient technique for myocardial gene delivery. Though the transfection efficiency can typically be enhanced if the naked DNA is coupled to compounds like liposomes, cholesterol-lipopolymers, poloaxime nanospheres and gelatin, these compounds do not enhance myocardial specificity (Lyon et al., 2008). Hence, naked DNA delivery to the heart must be carried out by direct intramyocardial injection (Müller et al., 2007) or by sonoporation or (UTMD) ultrasound targeted microbubble destruction, although transfection efficiency remains limiting (Dishart et al., 2003; Lyon et al., 2008).

Even though non-viral vectors and plasmid DNA are safe and relatively low cost, they only lead to transient transfection since they are unable to integrate into the host genome or persist in episomal forms. This makes them unsuitable for long-term gene expression as required in heart failure or hereditary cardiac diseases like cardiomyopathies, but they may be suitable for applications involving angiogenesis which is transient (Müller et al., 2007). These show that plasmid DNA is inefficient at myocardial gene delivery and expression (Lyon et al., 2008).

Four classes of viral vectors have predominantly been used for myocardial gene delivery: retroviral, lentiviral, adenoviral (Ad) and AAV vectors (Lyon et al., 2008). Among these, AAV has been proven to be more efficient compared to other vectors to transduce the heart. Adenoviral vectors have also been shown to transduce the heart whereas myocardial transduction with retroviral or lentiviral vectors is relatively inefficient. Most investigators have switched to AAV to achieve long-term expression and overcome inflammatory characteristics inherent to Ad (Sasano et al., 2007). No obvious pathology has been observed in connection with AAV (Gödecke et al., 2006) with consistent sustained expression of gene delivered by AAV vector for several months (Lyon et al., 2008).

AAV vectors allow long-term gene transfer to the heart in animal models, and skeletal muscle in humans but the specificity can be increased by transcriptional targeting (Goehringer et al., 2009). In the heart, AAV2 vectors utilize specific cell surface receptors including heparin sulphate proteoglycans, human fibroblast growth factor receptor 1, and integrins $\alpha v \beta 5/\alpha 5\beta 1$ to enter the cells via receptor-mediated endocytosis. They exploit the transcytosis trafficking pathway of endothelial cells, in order to cross the endothelial barrier to reach cardiomyocytes after intravascular delivery. The recombinant AAVs (rAAV), which are used for gene therapy do not integrate into the genome of cardiomyocyte but rather exist as episomal DNA (Lyon et al., 2008).

Among the 12 serotype classes of AAV currently identified, AAV1, AAV6, AAV8 and AAV9 have been observed to have higher tropism for myocardium than all the alternative candidate vectors for cardiac gene therapy. Also among these four, AAV9 was the most efficient vector for cardiac gene delivery (VandenDriessche et al., 2007). In mouse models, a 220-fold increase in myocardial transduction efficiency was obtained after only a single intravenous dose of AAV9 carrying a reporter gene was administered compared to the relatively cardiotropic AAV1 (Lyon et al., 2008).

Despite the success of using rAAV vectors for gene therapy, some obstacles still remain. The problem of neutralizing antibodies directed against the vector capsid is one major obstacle, which prevents re-administration of AAV vectors of the same serotype (Kwon et al., 2008). Moreover, T cell immune responses directed against the AAV capsid antigens presented in association with major histocompatibility complex class I antigens (MHC-I) on the surface of transduced target cells may curtail long-term gene expression. Other problems include limited tissue tropism for serotypes that bind heparan sulfate; poor infection of refractory cell types, such as stem cells; challenges with high-efficiency targeted gene delivery to specific cell populations (VandenDriessche et al., 2007); relatively restricted packaging capacity and inefficient large-scale production (Lyon et al., 2008); a relatively slow onset of gene expression, possibly owing to cytoplasmic trafficking, vector uncoating and conversion of the single-stranded genome into double-stranded DNA (Müller et al., 2007; Douar et al., 2001). A particular problem is achieving high expression levels that remain cardiac specific. While this can be done through the use of cardiac-specific promoters, drawbacks of these may include the large size of these promoters, since many vectors have a restricted cloning space, and/or the low activity compared to strong (viral) promoters, such as cytomegalovirus (CMV) or long teminal repeat (LTR) promoter sequences, widely used in gene therapy protocols.

To avoid transduction of other tissues, for instance skeletal muscle or liver (Yue et al., 2008, VandenDriessche et al., 2007), transcriptional targeting may be employed to increase the specificity of the vector for cardiac specific experimentation (Goehringer et al., 2009). Tissue specific promoters retain specificity and so are good promoters for viral vectors (Reynolds et al., 2001) since non-specific promoters can potentially elicit immune response against the vector plasmid (Cao et al., 2002) especially for intravenous vector application (Goehringer et al., 2009). It is also noted that tissue-specific promoters may also be considered inducible promoters because they may be induced by endogenous or exogenous factors as well (Venter et al., 2007). Many promoters have been used in gene therapy investigations for cardiac delivery, such as human cytomegalovirus (CMV) promoter (Fomicheva et al., 2008; Phillips et al., 2002), muscle creatine kinase (MCK) promoter, myosin light chain (MLC) 2v promoter (Gruber et al., 2004; Su et al., 2004), alpha myosin heavy chain promoter (Bostick et al., 2009; Black et al., 2002; Aikawa et al., 2002). Alpha myosin heavy chain (αMHC) promoter has been the most commonly used myocardial-specific promoter (Buerger et al., 2006) and has shown highly specific and robust levels of expression in the heart in most studies. The (MLC) 2v promoter has also been used by various cardiac gene therapy researchers but has been found to have a partial expression in the liver (Phillips et al., 2002; Su et al., 2004). Comparative study on five different tissue specific promoters in AAV9 vector has been conducted by Pacak et al., and the comparative analysis revealed that αMHC promoter confer the most cardiac specific expression (Pacak et al., 2008). The choice of promoters that has been used in the context of gene therapy vectors nevertheless remains relatively limited. Moreover, the robustness of many currently used heart specific promoters can still be augmented.

Increasing tissue-specific transgene expression is desirable as a way to decrease the amount of viral vector required to achieve a clinical effect. To increase activity, the use of cis-acting regulatory elements has been proposed. Typically, this concerns enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter. Some enhancers like CMV, αMHC, Rous sarcoma virus genome long terminal repeats (RSV), Simian virus (SV40), human phosphoglycerate kinase (PGK), and the muscle creatine kinase (MCK) are widely used in various vectors and transgenic animals (Xu et al., 2001; Wang et al., 2008; Salva et al., 2007). Most researchers have made use of the human CMV immediate-early enhancer to express a transgene (Xu et al., 2001; Gruh et al., 2008; Müller et al., 2000; Raake et al., 2008).

Sometimes, chimeric enhancer/promoters are constructed by swapping enhancer/promoter units from different sources for a greater effect. The most widely used of such a chimera is the CAG-promoter which results from a combination of CMV immediate-early enhancer, a chicken β-actin gene promoter and a rabbit β-globin splice acceptor or intron, making it drive strong gene expression in several tissues via viral or non-viral vectors (Xu et al., 2001; Wang et al., 2008). However, such enhancers do not increase specificity as they are not restricted to cardiac tissue.

To be able to provide a therapeutic level of the transgene product for an extended time period, gene transfer vectors preferably allow specifically regulated, high expression, while at the same time retaining sufficient cloning space for the transgene to be inserted, i.e., the regulatory elements used to achieve the high and tissue-specific expression preferably are of only limited length. However, none of the gene therapy vectors disclosed thus far satisfies all these criteria. Instead, gene therapy vectors are not sufficiently robust in terms of either expression levels and/or specificity of expression in the desired target cells, particularly cardiac cells. Decreasing the promoter/enhancer size often compromised the expression levels and/or expression specificity whereas the use of larger sequences often compromises the efficiency of gene delivery due to impaired vector function, packaging and/or transfection/transduction efficiency. Thus, there is a need in the art for vectors that achieve therapeutic levels of transgene expression in the heart for effective gene therapy.

SUMMARY OF THE DISCLOSURE

Disclosed is the increased efficiency of heart-specific expression of constructs used for gene therapy, particularly in vivo. At the same time, this is achieved using constructs with a high degree of structural compactness.

Therefore, rational approaches were used to design and select tissue-specific regulatory elements to arrive at potent tissue-specific promoters for highly efficacious gene delivery systems. By using multidisciplinary approaches involving a data-mining algorithm based on distance difference matrix (DDM) and rational in-silico design and analysis, potent heart-specific "regulons," which are highly enriched in cardiac transcription factor binding sites (TFBS) arranged in a particular chromosomal context were identified. These reguions in concert with a heart-specific promoter were shown to be potent cardiac-specific synthetic promoter/enhancers that dictate high-level cardiac-specific expression, also in vivo. Thus, provided are specific regulatory elements that enhance promoter expression, while retaining, or even reinforcing, tissue specificity.

Of particular importance is the small size of these regulatory elements, which makes it possible to accommodate this transcriptional control unit in any type of viral or non-viral vector, even in conjunction with large effector genes. Despite their limited length, the regulatory elements provided herein are able to enhance expression of a transgene to similar and typically even higher levels when compared to traditional, longer nucleic acid expression cassettes used in gene therapy.

Thus, according to a first aspect, nucleic acid regulatory elements of 700 nucleotides or less are provided for enhancing liver-specific gene expression, comprising a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof. According to a particular embodiment, the regulatory elements are even shorter, particularly 400 nucleotides or less, 300 nucleotides or less, even more particularly 250 nucleotides or less, most particularly 220 nucleotides or less or 200 nucleotides or less.

According to a further particular embodiment, the nucleic acid regulatory element comprises a sequence selected from the group consisting of: SEQ ID NO:1, SEQ ID NO:2, SEQ ID NO:3, a sequence having 95% identity to any of these sequences, or a functional fragment thereof. According to yet a further particular embodiment, the nucleic acid regulatory element comprises SEQ ID NO:1, a sequence having 95% identity to any of these sequences, or a functional fragment thereof. According to an alternative embodiment, the nucleic acid regulatory element comprises SEQ ID NO:5, sequence having 95% identity to any of these sequences, or a functional fragment thereof.

According to an alternative embodiment, nucleic acid regulatory elements are provided of 600 nucleotides or less hybridizing under stringent conditions to the regulatory element comprising a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof.

According to a further alternative embodiment, nucleic acid regulatory elements of 600 nucleotides or less are provided, comprising at least two fragments of sequences selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a sequence having 95% identity to any of these sequences. According to a further particular embodiment, at least two of these fragments are different from each other. According to yet a further particular embodiment, all fragments are different from each other. According to an alternative particular embodiment, at least two fragments are identical. According to another specific embodiment, at least one of the at least two fragments is a functional fragment. According to a further specific embodiment, all fragments are functional fragments of the listed sequences.

In a further aspect, the regulatory elements are used to express genes or transgenes. Accordingly, nucleic acid expression cassettes are provided comprising a nucleic acid regulatory element as described herein, operably linked to a promoter. According to a further embodiment of this aspect, the nucleic acid regulatory element in the nucleic acid expression cassettes is operably linked to a promoter and a transgene.

According to a specific embodiment, the nucleic acid expression cassettes are provided with two or more nucleic acid regulatory elements. These two or more nucleic acid regulatory elements are then operably linked to the promoter, and optionally the transgene. According to a further specific embodiment, at least two of the two or more regulatory elements are identical or substantially identical (e.g., 90% or 95% identical). According to yet a further specific embodiment, all of the two or more regulatory elements are identical or substantially identical. According to an alternative specific embodiment, at least two of the two or more regulatory elements are not identical to each other.

According to a particular embodiment, the promoter contained in the nucleic acid expression cassettes provided is a cardiac-specific promoter. According to a further particular embodiment, the cardiac-specific promoter is from the myosin heavy chain gene. According to yet a further particular embodiment, the myosin heavy chain promoter is from the myosin heavy chain α (αMHC), most particularly the 363 bp promoter as defined in Pacak et al., 2008.

According to another particular embodiment, the nucleic acid expression cassettes provided additionally contain a β-globin intron.

The transgene that may be contained in the nucleic acid expression cassette typically encodes a gene product, such as RNA or a polypeptide (protein). According to a specific embodiment, the transgene encodes a therapeutic protein. According to a further specific embodiment, the therapeutic protein is selected from the group of angiogenic factors (such as VEGF or PlGF), ATPases (such as SERCA2a), ion channels, cytokines and growth factors.

The nucleic acid expression cassette, and even the regulatory element, as described herein, may be used as such. However, in typical embodiments, the expression cassette will be part of a nucleic acid vector. Accordingly, in a further aspect vectors are provided comprising the regulatory element, as described herein. According to a particular embodiment, the vectors comprise the nucleic acid expression cassette as disclosed in the application.

According to a specific embodiment, the vectors provided are viral vectors, in particular retroviral, lentiviral, adenoviral or AAV vectors, more in particular lentiviral or AAV vectors. According to particularly envisaged embodiments, the vectors are AAV vectors, such as AAV9 or AAV2/9. According to an alternative embodiment, the vectors are non-viral vectors. According to yet another alternative embodiment, the vectors contain both viral and non-viral elements.

It is evident to the skilled person that the cardiac-specific regulatory elements, the nucleic acid expression cassettes and the vectors containing either may be used for gene therapy purposes. Accordingly, the use of the nucleic acid regulatory element, as described herein, in gene therapy is envisaged. According to another particular embodiment, use of the nucleic acid expression cassettes, as disclosed herein, in gene therapy is disclosed. According to yet a further particular embodiment, the application envisages the use of vectors, as described herein, for gene therapy. According to a particular embodiment, the gene therapy envisaged is cardiac-specific gene therapy. According to another particular embodiment, the gene therapy is gene therapy for a disease originating in the heart.

In a further aspect, methods for expressing a transgene product in heart cells are provided, comprising the steps of:

introducing in heart cells the nucleic acid expression cassette wherein a nucleic acid regulatory element, as described herein, is operably linked to a promoter and a transgene;
expressing the transgene product in the heart cells.

According to a further particular embodiment, the transgene product is a protein. According to yet a further particular embodiment, the protein is a therapeutic protein. According to an alternative embodiment, the transgene product is RNA, e.g., miRNA or siRNA. According to another particular embodiment, the methods are performed in vitro. According to an alternative particular embodiment, the methods are performed ex vivo. According to an alternative particular embodiment, the methods are performed in vivo.

Methods of gene therapy for a subject in need thereof are also provided herein. These methods typically comprise the steps of:
introducing in the heart of the subject a nucleic acid expression cassette wherein a nucleic acid regulatory element, as described herein, is operably linked to a promoter and a transgene encoding a therapeutic protein;
expressing a therapeutic amount of the (therapeutic) protein in the heart.

Instead of introducing the nucleic acid expression cassette as such, the methods may also introduce in the heart of the subject a vector containing a nucleic acid expression cassette wherein a nucleic acid regulatory element, as described herein, is operably linked to a promoter and a transgene encoding a therapeutic protein. Several diseases can be envisaged for treatment with gene therapy (e.g., angiogenesis defects, heart failure, etc.), examples will be given in the application.

In general, the subject in need thereof, will be a mammal, most particularly a human. Typically, the subject in need thereof, will have certain symptoms, most particularly symptoms characteristic of a disease. According to a further particular embodiment, the methods additionally comprise the step of ameliorating the symptoms of the subject in need thereof, by expressing the therapeutic amount of the therapeutic protein.

BRIEF DESCRIPTION OF THE FIGURES

FIG. 1. Transcription factor binding sites of the alpha-myosin heavy chain enhancer/promoter (α-MHC) (Catalogue of Regulatory Elements—at worldwide web cbil.upenn.edu/MTIR/MHCa-sites.html#MARKER-MHCa_seq1)

DETAILED DESCRIPTION

Definitions

Figure 2:
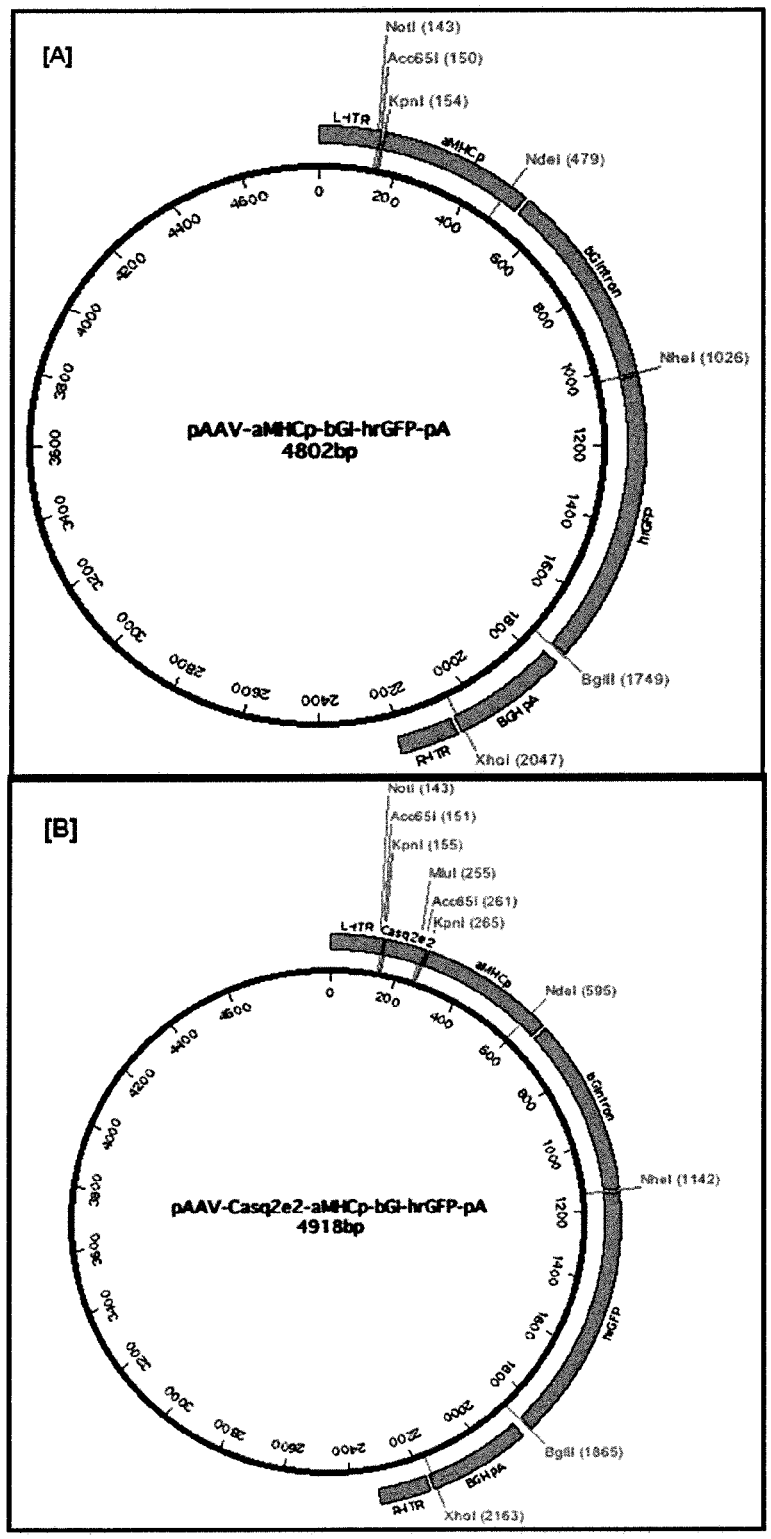
FIG. 2. Plasmid vectors generated from theoretical sequences using MacVector software tools. The various elements were cloned using the respective restriction sites. The hrGFP was the first to be cloned followed by the αMHCp. The β-globin intron was finally cloned to generate the pAAV-αMHCp-βGI-hrGFP-pA [A]. The plasmid was then sequenced and subsequently the regulons were cloned at the Acc65I cloning site in plasmid [A] to generate the pAAV-Reg-αMHCp-βGI-hrGFP-pA. Each plasmid with a regulon was named. Each newly generated construct with the respective regulon were designated after the name of the regulon. For example, cloning Casq2e2 regulon into the pAAV-αMHCp-βGI-hrGFP-pA plasmid, gave rise to pAAV-Casq2e2-αMHCp-βGI-hrGFP-pA [B]. Each cloning was followed by screening to select positive clones from colonies that arose from bacterial transformation. Reg corresponds to regulon (Myl3, Brd7, Myl2, Casq2e1, Casq2e2, Ankrd1e1, Ankrd1e2, and Ankrd1e3). aMHCp and bGIntron (βGI) correspond to αMHCp and β-globin intron, respectively.

The disclosure will be described with respect to particular embodiments and with reference to certain drawings but it is not limited thereto, but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g., "a," "an," and "the," this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments hereof are capable of operation in other sequences than described or illustrated herein.

The following terms or definitions are provided solely to aid in the understanding hereof Unless specifically defined herein, all terms used herein have the same meaning as they would to one skilled in the art of the disclosure. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

A "regulatory element," as used herein, refers to transcriptional control elements, in particular non-coding cis-acting transcriptional control elements, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a cardiac-specific transcription factor. Typically, regulatory elements, as used herein, increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g., in the promoter region) or downstream (e.g., in the 3'UTR) of the gene they regulate in vivo, and may be located in the immediate vicinity of the gene or further away. Of note, although regulatory elements, as disclosed herein, typically are naturally occurring sequences, combinations of (parts of) such regulatory elements or several copies of a regulatory element, i.e., non-naturally occurring sequences, are themselves also envisaged as regulatory element. Regulatory elements, as used herein, may be part of a larger sequence involved in transcriptional control, e.g., part of a promoter sequence. However, regulatory elements alone are typically not sufficient to initiate transcription, but require a promoter to this end.

"Cardiac-specific expression" or "heart-specific expression," as used in the application, refers to the preferential or predominant expression of a (trans)gene (as RNA and/or polypeptide) in the heart (or cardiac tissue) as compared to other tissues. According to particular embodiments, at least 50% of the (trans)gene expression occurs within the heart. According to more particular embodiments, at least 60%, at least 70%, at least 75%, at least 80%, at least 85%, at least 90%, at least 95%, at least 97%, at least 99% or 100% of the (trans)gene expression occurs within the heart. According to a particular embodiment, heart-specific expression entails that there is no "leakage" of expressed gene product to other organs, such as liver, non-cardiac muscle, lung, kidney and/or spleen. Thus, according to particular embodiments, less than 10%, less than 5%, less than 2% or even less than 1% of the (trans)gene expression occurs in an organ or tissue other than the heart. The same applies mutatis mutandis for cardiomyocyte-specific expression, which may be considered as a particular form of heart-specific expression. Throughout the application, where cardiac-specific is mentioned in the context of expression, cardiomyocyte-specific expression is also explicitly envisaged. Similarly, where tissue-specific expression is used in the application, cell-type specific expression of the cell type(s) predominantly making up the tissue is also envisaged.

The term, "functional fragment," as used in the application, refers to fragments of the sequences, disclosed herein, that retain the capability of regulating heart-specific expression, i.e., they still confer tissue specificity and they are capable of regulating expression of a (trans)gene in the same way (although possibly not to the same extent) as the sequence from which they are derived. Fragments comprise at least 10 contiguous nucleotides from the sequence from which they are derived. In further particular embodiments, fragments comprise at least 15, at least 20, at least 25, at least 30, at least 35 or at least 40 contiguous nucleotides from the sequence from which they are derived.

The term "hybridize under stringent conditions," and grammatical equivalents thereof, refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature ($T_m$) of the native duplex. Methods of calculating $T_m$ are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours. (See, generally, Sambrook et al., Molecular Cloning: A Laboratory Manual, 2nded., Cold Spring Harbor Press, 1987; Ausubel et al., Current Protocols in Molecular Biology, Greene Publishing, 1987).

As used herein, the term "nucleic acid expression cassette" refers to nucleic acid molecules that include one or more transcriptional control elements (such as, but not limited to, promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid sequence is inserted.

The term "operably linked," as used herein, refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

As used in the application, the term "promoter" refers to nucleic acid sequences that regulate, either directly or indirectly, the transcription of corresponding nucleic acid coding sequences to which they are operably linked (e.g., a transgene or endogenous gene). A promoter may function alone to regulate transcription or may act in concert with one or more other regulatory sequences (e.g., enhancers or silencers). In the context hereof, a promoter is typically operably linked to regulatory elements to regulate transcription of a transgene. When a regulatory element, as described herein, is operably linked to both a promoter and a transgene, the regulatory element can (1) confer a significant degree of cardiac specific expression in vivo (and/or in cardiomyocytes/heart-derived cell lines in vitro) of the transgene, and/or (2) can increase the level of expression of the transgene in the heart (and/or in cardiomyocytes/heart cell lines in vitro). A "minimal promoter," as used herein, is part of a full-size promoter still capable of driving expression, but lacking at least part of the sequence that contributes to regulating (e.g., tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Minimal promoters have been extensively documented in the art, a non-limiting list of minimal promoters is provided in the specification.

The term "transgene," as used herein, refers to particular nucleic acid sequences encoding a polypeptide or a portion of a polypeptide to be expressed in a cell into which the nucleic acid sequence is inserted. However, it is also possible that transgenes are expressed as RNA, typically to control (e.g., lower) the amount of a particular polypeptide in a cell into which the nucleic acid sequence is inserted. These RNA molecules include but are not limited to, molecules that exert their function through RNA interference (shRNA, RNAi), micro-RNA regulation (miR) (which can be used to control expression of specific genes), catalytic RNA, antisense RNA, RNA aptamers, etc. How the nucleic acid sequence is introduced into a cell is not essential, it may, for instance, be through integration in the genome or as an episomal plasmid. Of note, expression of the transgene may be restricted to a subset of the cells into which the nucleic acid sequence is inserted. The term "transgene" is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By "mutant form" is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

The term "vector," as used herein refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The term "vector" may thus also be defined as a gene delivery vehicle that facilitates gene transfer into a target cell. This definition includes both non-viral and viral vectors. Non-viral vectors include, but are not limited to, cationic lipids, liposomes, nanoparticles, PEG, PEI, etc. Viral vectors are derived from viruses and include, but are not limited to, retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g., a cancer cell, and are typically used to trigger the (cancer) cell-specific (onco)lysis.

According to a first aspect, nucleic acid regulatory elements for enhancing liver-specific gene expression are provided of 700 nucleotides or less, particularly 600 nucleotides or less, comprising a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8. According to a specific embodiment, the nucleic acid regulatory elements comprise a sequence having 80% sequence identity, more in particular 85% sequence identity, even more in particular 90% sequence identity, yet even more in particular 95%, 98% or 99% sequence identity to any of these sequences. According to another specific embodiment, the nucleic acid regulatory elements comprise a functional fragment of these sequences (or of the sequences sharing high percentage sequence identity with these sequences). How the sequences involved in heart-specific gene expression were identified is outlined in the examples section.

It is a considerable benefit that the regulatory elements, as described herein, are fully functional while being only of limited length. This allows their use in vectors or nucleic acid expression cassettes without unduly restricting their payload capacity. Accordingly, the nucleic acid regulatory elements are 700 nucleotides or less in length, 600 nucleotides or less in length, 550 nucleotides or less, 500 nucleotides or less, 450 nucleotides or less, more in particular 400 nucleotides or less, 350 nucleotides or less, 300 nucleotides or less, yet even more in particular 250 nucleotides or less, 200 nucleotides or less, 175 nucleotides or less, 150 nucleotides or less, 125 nucleotides or less, 110 nucleotides or less, 100 nucleotides or less, 90 nucleotides or less, 80 nucleotides or less, 75 nucleotides or less, 70 nucleotides or less, 65 nucleotides or less, 60 nucleotides or less, 55 nucleotides or less, 50 nucleotides or less. However, it is to be understood that the disclosed nucleic acid regulatory elements retain regulatory activity (i.e., with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 120 nucleotides, 135 nucleotides or even 150 nucleotides.

Furthermore, according to particular embodiments, the nucleic acid regulatory elements of 600 nucleotides or less for enhancing liver-specific gene expression consist essentially of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof. That is to say, the regulatory element may, for instance, additionally comprise sequences used for cloning purposes (see for an arbitrary example the sequences provided as SEQ IDs 9-16), but the aforementioned sequences make up the essential part of the regulatory element, e.g., they do not form part of a larger regulatory region, such as a promoter. According to a further particular embodiment, the nucleic acid regulatory elements of 600 nucleotides or less for enhancing liver-specific gene expression consist of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof.

The nucleic acid sequences may be provided as DNA or RNA, as double stranded or single stranded molecule. In case the sequences are provided as single stranded nucleic acids, the complement strand is considered equivalent to the disclosed SEQ IDs, and is also envisaged for use in the nucleic acid constructs and methods and uses thereof, described herein. Thus, according to a specific embodiment, the nucleic acid regulatory elements comprise the complement strand of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or of a functional fragment thereof. According to a further specific embodiment, the regulatory elements consist essentially of the complement strand of the aforementioned sequences. According to yet a further specific embodiment, the regulatory elements consist of the complement strand of the listed sequences.

Furthermore, it is envisaged that sequences hybridizing to the sequences listed herein, in particular hybridizing to the complement of the sequences disclosed herein, can also be used as nucleic acid regulatory elements. With hybridizing is typically meant "hybridizing under stringent conditions." Sequences hybridizing to the listed sequences do not need to be of equal length as the sequence they hybridize to. However, it is to be noted that these hybridizing sequences, to be used as nucleic acid regulatory elements, particularly do not exceed the size limit for the regulatory elements, as described herein. Moreover, according to a specific embodiment, the size of the nucleic acid hybridizing to SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof, does not differ more than 25% in length, in particular 20% in length, more in particular 15% in length, most in particular not more than 10% in length from the sequence it hybridizes to.

Several of the sequences, disclosed herein, are very limited in length; some are also considerably shorter than others. Thus, particularly for the shorter sequences, it is possible to make a regulatory element that comprises two or more copies of the same sequence, or even two different sequences of the listed sequences. Although modularly combining sequences (or copies of the same sequence) is of course possible for all sequences, it is particularly envisaged for those combinations of sequences that do not exceed the size of the regulatory element as defined herein, i.e., do not exceed 700 nucleotides (or more in particular do not exceed 600 nucleotides or even more in particular do not exceed 500 or 450 nucleotides).

According to a very specific embodiment, nucleic acid regulatory elements, disclosed herein, comprise at least two functional fragments of the listed sequences, combined to make a new (artificial) regulatory sequence. According to a further specific embodiment, these at least two functional fragments are non-identical fragments. According to an alternative embodiment, at least two of the at least two functional fragments are identical to each other. According to another very specific embodiment, two fragments of the listed sequences, at least one of which is not functional as such, are combined to make a new (artificial) regulatory sequence.

Sequences disclosed herein, are regulatory sequences controlling transcription of heart-specific genes in vivo, in particular controlling the following genes: calsequestrin 2 (cardiac muscle) also known as PDIB2, FLJ26321, FLJ93514 or CASQ2 (CASQ2; GeneID 845 for the human gene); ankyrin repeat domain 1 (cardiac muscle) also known as cardiac ankyrin repeat protein; cytokine inducible nuclear protein; liver ankyrin repeat domain 1 (ANKRD1; GeneID 27063 for the human gene); myosin, light chain 2, regulatory, cardiac, slow (MYL2; GeneID 4633 for the human gene); myosin, light chain 3, alkali; ventricular, skeletal, slow (MYL3; GeneID 4634 for the human gene); bromodomain containing 7, also known as BP75, CELTIX1, NAG4 (BRD7; GeneID 29117 for the human gene). According to a specific embodiment, the regulatory elements comprise CASQ2 regulatory elements, i.e., regulatory elements that control expression of the CASQ2 gene in vivo, in particular SEQ ID NO:1. According to alternative (but not exclusive) specific embodiments, the regulatory elements comprise ANKRD1 regulatory sequences, in particular SEQ ID NO:5.

As elaborated herein, regulatory sequences are typically enriched in cardiac-specific transcription factor binding sites. According to specific embodiments, hypoxia responsive elements (HRE) are not envisaged as a regulatory sequence, as used herein. This is because these elements typically act as switches and only enhance expression in hypoxic conditions (Phillips et al., 2002). Of course, for alternative embodiments where it would be desirable to only enhance expression in hypoxic conditions, including HRE as regulatory elements may still be envisaged.

The nucleic acid regulatory elements, disclosed herein, can be used in a nucleic acid expression cassette. Thus, according to one aspect, nucleic acid expression cassettes are provided wherein a regulatory element, as described herein, is operably linked to a promoter. According to a further embodiment, the regulatory element is operably linked to a promoter and a transgene.

As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this need not be the case in vivo. E.g., a regulatory element sequence naturally occurring downstream of a gene whose transcription it affects is able to function in the same way when located upstream of the promoter. Thus, according to a specific embodiment, the regulatory or enhancing effect of the regulatory sequences is position-independent. Moreover, the regulatory sequences are able to exert their effect on expression independent of particular promoter or gene sequences.

Thus, they can be used in nucleic acid expression cassettes in conjunction with their natural promoter, as well as with another promoter. Although the enrichment in cardiac-specific TFBS in principle allows the regulatory elements to direct tissue-specific expression even from a promoter that itself is not heart-specific (or lacks elements, which contribute to making it liver-specific, in the case of minimal promoters), cardiac-specific promoters are particularly envisaged. This to increase cardiac-specificity and/or avoid leakage of expression in other tissues. The heart-specific promoter may or may not be a cardiomyocyte-specific promoter. The promoter does not need to be the promoter of the transgene in the nucleic acid expression cassette, although it is possible that the transgene is transcribed from its own promoter. According to a particular embodiment, the nucleic acid expression cassette is used for gene therapy. According to this embodiment, the promoter may be homologous (i.e., from the same species as the animal (in particular mammal) to be transfected with the nucleic acid expression cassette) or heterologous (i.e., from a source other than the species of the mammal to be transfected with the expression cassette). As such, the source of the promoter may be any virus, any unicellular prokaryotic or eukaryotic organism, any vertebrate or invertebrate organism, or any plant, or may even be a synthetic promoter (i.e., having a non-naturally occurring sequence), provided that the promoter is functional in combination with the regulatory elements, described herein. According to a specific embodiment, the promoter is a mammalian promoter, in particular a murine or human promoter. According to a further specific embodiment, the promoter is a mammalian heart-specific promoter. According to yet a further specific embodiment, the promoter is a human heart-specific promoter. According to an alternative embodiment, the promoter is a viral promoter. According to a further embodiment, the viral promoter is a heart-specific viral promoter. The promoter may be an inducible or constitutive promoter.

To minimize the length of the nucleic acid expression cassette, it is particularly envisaged that the regulatory elements are linked to minimal promoters, or shortened versions of a cardiac-specific promoter. According to a particular embodiment, the promoter used is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less. Examples of promoters that may be used include, but are not limited to, human cytomegalovirus (CMV) promoter, muscle creatine kinase (MCK) promoter, myosin light chain (MLC) promoter, in particular MLC2, myosin heavy chain (MHC) promoter, in particular alpha-MHC, desmin promoter, cardiac troponin C promoter. Several of these promoters are described in Pacak et al., 2008. Any of these promoters may also be used as a minimal promoter, which have been described in the art. Sometimes minimal promoters are referred to as basal or core promoters. Although these may differ somewhat with regard to which sequences are lacking in the promoter, all such promoters lacking (part of) their regulatory sequences are envisaged within the definition of minimal promoters. A particularly envisaged minimal promoter is the alpha-MHC minimal promoter, more particularly the 363 bp sequence as defined in Pacak et al., 2008; or the promoters as depicted in FIG. 1.

The regulatory sequences, as disclosed herein, may be used in the nucleic acid expression cassettes. According to a particular embodiment, only one regulatory element is included in the expression cassette. According to an alternative particular embodiment, more than one regulatory element is included in the nucleic acid expression cassette, i.e., they are combined modularly to enhance their regulatory (and/or enhancing) effect. According to a further particular embodiment, two or more copies of the same regulatory element are used in the nucleic acid expression cassette. For instance, 2, 3, 4, 5, 6, 7, 8, 9, 10 copies of a regulatory element may be provided as tandem repeats. According to another further particular embodiment, the more than one regulatory element included in the nucleic acid expression cassette comprises at least two different regulatory elements. Both embodiments are not mutually exclusive, it is possible to combine both identical and non-identical regulatory elements with each other in the nucleic acid expression cassettes, described herein. Since the combination of regulatory elements will function as one regulatory element in the nucleic acid expression cassette, this embodiment is largely equivalent to the combinations of sequences in one regulatory element. However, as each of the sequences functions as regulatory element as such, it is preferred to refer to them as a combination of regulatory sequences, and to nucleic acid expression cassettes containing more than one regulatory sequence. Although in theory there is no upper limit to the number of regulatory elements that can be included in the expression cassette (other than the feasibility of cloning), it is according to one embodiment particularly envisaged that the length of the total regulatory element(s) in the nucleic acid expression cassette does not exceed 1000 nucleotides. According to further particular embodiments, the total length of the regulatory elements does not exceed 900 nucleotides, 800 nucleotides, 750 nucleotides, 700 nucleotides, 600 nucleotides, 550 nucleotides, 500 nucleotides, 450 nucleotides, 400 nucleotides, 350 nucleotides, 300 nucleotides, 250 nucleotides, 200 nucleotides, 175 nucleotides, 150 nucleotides, 125 nucleotides, 110 nucleotides, 100 nucleotides, 90 nucleotides, 80 nucleotides, 75 nucleotides, 70 nucleotides, 65 nucleotides, 60 nucleotides, 55 nucleotides or 50 nucleotides. However, the minimal length defined for the regulatory elements also applies to regulatory elements, or combinations thereof, used in nucleic acid expression cassettes.

As the payload of the nucleic acid expression cassette is influenced both by promoter and regulatory element(s), it is envisaged that according to a particular embodiment, the total length of the promoter and regulatory elements in the nucleic acid expression cassette is 1000 nucleotides or less, 900 nucleotides or less, 800 nucleotides or less, 750 nucleotides or less, 700 nucleotides or less, 600 nucleotides or less, 550 nucleotides or less, 500 nucleotides or less, 450 nucleotides or less, 400 nucleotides or less, 350 nucleotides or less, 300 nucleotides or less, or even 250 nucleotides or less.

According to a very specific embodiment, the nucleic acid regulatory elements are the only regulatory (and/or enhancing) elements in the nucleic acid expression cassette, there are, e.g., no regulatory elements present any more in the promoter, or no additional enhancers in the construct. According to a further specific embodiment, the sequences selected from the group of SEQ ID NO:1, SEQ ID NO:2, SEQ ID NO:3, SEQ ID NO:4, SEQ ID NO:5, SEQ ID NO:6, SEQ ID NO:7, SEQ ID NO:8, a sequence having 95% identity to any of these sequences, or a functional fragment thereof, are the sole regulatory (and/or enhancing) sequences present in either the regulatory element or the nucleic acid expression cassette, i.e., the regulatory element does not contain other regulatory or enhancing sequences.

As already indicated, the regulatory sequences are able to exert their effect on expression independent of particular promoter or (trans)gene sequences. The nature of the (trans) gene accordingly is not vital hereto, as long as the operably linked promoter and regulatory element are successful in transcribing the sequence. According to particular embodiments, the nucleic acid expression cassettes will be used in gene therapy, and the transgene will be primarily expressed in the heart. In some cases, the gene product may also be secreted into the bloodstream after synthesis. Thus, included within the scope of this application is any transgene encoding a nucleic acid (e.g., RNA) and/or a polypeptide to be circulated in the blood.

The transgene may be homologous or heterologous to the promoter (and/or to the animal, in particular mammal, in which it is introduced, in cases where the nucleic acid expression cassette is used for gene therapy). In addition, the transgene may be a full length cDNA or genomic DNA sequence, or any fragment, subunit or mutant thereof that has at least some biological activity. In particular, the transgene may be a minigene, i.e., a gene sequence lacking part, most or all of its intronic sequences. The transgene, thus optionally, may contain intron sequences. Optionally, the transgene may be a hybrid nucleic acid sequence, i.e., one constructed from homologous and/or heterologous cDNA and/or genomic DNA fragments. The transgene may also optionally be a mutant of one or more naturally occurring cDNA and/or genomic sequences.

The transgene may be isolated and obtained in suitable quantity using one or more methods that are well known in the art. These methods and others useful for isolating a transgene are set forth, for example, in Sambrook et al., (supra) and in Berger and Kimmel (Methods in Enzymology: Guide to Molecular Cloning Techniques, vol. 152, Academic Press, Inc., San Diego, Calif. (1987)).

The use of transgene mutant sequences is also contemplated in the application. A mutant transgene is a transgene containing one or more nucleotide substitutions, deletions, and/or insertions as compared to the wild-type sequence. The nucleotide substitution, deletion, and/or insertion can give rise to a gene product (i.e., e., protein or RNA) that is different in its amino acid/nucleic acid sequence from the wild-type amino acid/nucleic acid sequence. Preparation of such mutants is well known in the art.

According to a particular embodiment, the product encoded by the transgene is a protein. According to a further particular embodiment, the product is a therapeutic protein.

A non-exhaustive and non-limiting list of transgenes (and therapeutic proteins) envisaged in the application includes angiogenic factors for therapeutic angiogenesis, such as VEGF, PlGF, or guidance molecules, such as ephrins, semaphorins, Slits and netrins or their cognate receptors; cytokines and/or growth factors, such as erythropoietin (EPO), interferon-$\alpha$, interferon-$\beta$, interferon-$\gamma$, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), proteins involved in calcium handling, such as SERCA (Sarco/Endoplasmic Reticulum Ca2+-ATPase), calcineurin, transgenes encoding antibodies, nanobodies, anti-viral dominant-negative proteins, and fragments, subunits or mutants thereof.

According to a very specific embodiment, the nucleic acid expression cassette does not contain a transgene, but the regulatory element(s) operably linked to the promoter are used to drive expression of an endogenous gene (that thus is equivalent to the transgene in terms of enhanced and/or tissue-specific expression). The nucleic acid expression cassette may be integrated in the genome of the cell or stay episomal.

Other sequences may be incorporated in the nucleic acid expression cassette as well, typically to further increase or stabilize the expression of the transgene product (e.g., introns and/or polyadenylation sequences). Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal.

According to particular embodiments, the nucleic acid expression cassette contains a β-globin intron. Beta-globin intron (betaIVS-II) derived from the human beta-globin gene is essential for the accumulation of stable cytoplasmic mRNA and it is implicated in promoting efficient 3'-end formation— for efficient 3'-end cleavage and polyadenylation. The beta-globin gene has two intronic sequences, IVS-I and IVS-II, each of which can restore expression of an intronless gene. IVS is necessary for correct and efficient 3'-end formation, without which transcription would results in low levels of mRNA (Antoniou et al., 1998).

Any polyadenylation signal that directs the synthesis of a poly A tail is useful in the expression cassettes described herein, examples of those are well known to one of skill in the art (e.g., the bovine growth hormone polyadenylation signal). Others include, but are not limited to, polyA sequences derived from the SV40 late gene, and the minimal rabbit β-globin (mRBG) gene (Xu et al., 2001).

The expression cassettes described in the application can be used, for example, to express proteins that are normally expressed and utilized in the heart, or to express proteins that are expressed in the heart and are then exported to the blood stream for transport to other portions of the body. Thus, according to some particular embodiments, the expression cassettes hereof can be used to express a therapeutic amount of a polypeptide (or other gene product, such as RNA) to ameliorate the symptoms of a disease. Typically, the gene product is encoded by the coding sequence within the expression cassette (i.e., the transgene), although in principle it is also possible to increase expression of an endogenous gene. A "therapeutic amount," as used herein, is an amount that ameliorates the symptoms of a disease. Such amount will typically depend on the gene product and the severity of the disease, but can be decided by the skilled person, possibly through routine experimentation.

According to particular embodiments, the amount of gene product expressed when using an expression cassette, as described herein, (i.e., with at least one cardiac-specific enhancer) are higher than when an identical expression cassette is used but without an enhancer sequence therein. More particularly, the expression is at least double as high, at least five times as high, at least ten times as high, at least 20 times as high, at least 30 times as high, at least 40 times as high, most particularly at least 50 times as high, or even at least 60 times as high as when compared to the same construct without enhancer (see e.g., FIG. 11). According to further embodiments, the higher expression remains specific to the heart.

According to a particular embodiment, the expression cassettes described in this application direct the expression of a therapeutic amount of the gene product encoded by the coding sequence for an extended period. Indeed, as long as therapeutic levels are achieved, no new treatment is necessary. Typically, therapeutic expression is envisaged to last at least 20 days, at least 50 days, at least 100 days, at least 200 days, and in some instances 300 days or more. Expression of the gene product (e.g., polypeptide) encoded by the coding sequence can be measured by any art-recognized means, such as by antibody-based assays, e.g., a Western Blot or an ELISA assay, for instance, to evaluate whether therapeutic expression of the gene product is achieved. Expression of the gene product may also be measured in a bioassay that detects an enzymatic or biological activity of the gene product.

In a further aspect, provided are vectors that include a regulatory element, as described herein. According to a further particular embodiment, the vectors contain an expression cassette, as described herein. The vectors can be episomal vectors (i.e., that do not integrate into the genome of a host cell), or can be vectors that integrate into the host cell genome. Examples of episomal vectors include (extrachromosomal) plasmids and so-called mini-circles, which are composed of the expression cassette only and are devoid of bacterial sequences, and examples of vectors that integrate into the host cell genome include viral vectors.

Representative plasmid vectors include pUC vectors, bluescript vectors (pBS) and pBR322 or derivatives thereof, that are devoid of bacterial sequences (minicircles). Some of the plasmid vectors can be adapted to incorporate elements that enhance episomal plasmid persistence in the transfected cells. Such sequences include S/MARs that correspond to scaffold/matrix attached region modules linked to a transcription unit (Jenke et al., 2004; Manzini et al., 2006).

Representative viral vectors include vectors derived from adeno-associated virus, adenovirus, retroviruses and lentiviruses. Alternatively, gene delivery systems can be used to combine viral and non-viral components, such as nanoparticles or virosomes (Yamada et al., 2003).

Retroviruses and lentiviruses are RNA viruses that have the ability to insert their genes into host cell chromosomes after infection. Retroviral and lentiviral vectors have been developed that lack the genes encoding viral proteins, but retain the ability to infect cells and insert their genes into the chromosomes of the target cell (Miller, 1990; Naldini et al., 1996). The difference between a lentiviral and a classical Moloney-murine leukemia-virus (MLV) based retroviral vector is that lentiviral vectors can transduce both dividing and non-dividing cells whereas MLV-based retroviral vectors can only transduce dividing cells.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and non-dividing cells in many different tissues in vivo including airway epithelial cells, endothelial cells, hepatocytes and various tumors (Trapnell, 1993).

Adeno-associated virus (AAV) is a small ssDNA virus which infects humans and some other primate species, not known to cause disease and consequently causing only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited.

Another viral vector is derived from the herpes simplex virus, a large, double-stranded DNA virus. Recombinant forms of the vaccinia virus, another dsDNA virus, can accommodate large inserts and are generated by homologous recombination.

According to a particular embodiment, the vector is a viral vector. According to further particular embodiments, the vector is an AAV vector. According to alternative embodiments, the vector is a lentiviral vector. As the AAV9 serotype was shown to exhibit superior cardiotropism in comparison to other AAV types (VandenDriessche et al., 2007), particularly envisaged is the use of AAV9 or AAV2/9 vectors.

In a further particular aspect, the nucleic acid regulatory elements, the nucleic acid expression cassettes and the vectors, described herein, can be used in gene therapy. Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

According to a particular embodiment, the use of the nucleic acid regulatory elements, nucleic acid expression cassettes or vectors, as described herein, is envisaged for gene therapy of heart cells. According to a further particular embodiment, the use of the regulatory elements, expression cassettes or vectors is for gene therapy in vivo.

Gene transfer into mammalian cardiomyocytes may be performed using both ex vivo and in vivo procedures. The ex vivo approach requires harvesting of the heart cells, in vitro transduction with long-term expression vectors, and reintroduction of the transduced cardiomyocytes into the circulation. In vivo targeting is however more envisaged, typically via intravenous or intra-arterial administration.

It is understood by the skilled person that the use of the cardiac-specific enhancers, expression cassettes and vectors obviously has implications beyond gene therapy, e.g., coaxed differentiation of stem cells into cardiomyogenic cells, transgenic models for over-expression of proteins in the heart, models for cardiotoxicity screening, etc.

According to a further aspect, methods for expressing a protein in cardiac cells are provided, comprising the steps of introducing in heart cells a nucleic acid expression cassette (or a vector), as described herein, and expressing the transgene protein product in the cardiac cells. These methods may be performed both in vitro and in vivo.

Methods of gene therapy for a subject in need thereof, are also provided, comprising the steps of introducing in the heart of the subject a nucleic acid expression cassette containing a transgene encoding a therapeutic protein, and expressing a therapeutic amount of the therapeutic protein in the heart.

According to a further embodiment, the method comprise the steps of introducing in the heart of the subject a vector comprising the nucleic acid expression cassette containing a transgene encoding a therapeutic protein, and expressing a therapeutic amount of the therapeutic protein in the heart.

According to another aspect, a pharmaceutical composition is provided comprising a nucleic acid expression cassette containing a transgene encoding a therapeutic protein, and a pharmaceutically acceptable carrier. According to another embodiment, the pharmaceutical composition comprises a vector containing the nucleic acid expression cassette containing a transgene encoding a therapeutic protein, and a pharmaceutically acceptable carrier.

The pharmaceutical composition may be provided in the form of a kit.

The use of regulatory elements, as disclosed herein, for the manufacture of these pharmaceutical compositions is also envisaged.

It is to be understood that although particular embodiments, specific constructions and configurations, as well as materials, have been discussed herein, for embodiments of the disclosure, various changes or modifications in form and detail may be made without departing from the scope and spirit hereof. The following examples are provided to better illustrate particular embodiments, and they should not be considered limiting the application. The application is limited only by the claims.

EXAMPLES

Materials and Methods

Identification of Regulons

A novel validated data mining algorithm called the Distance Difference Matrix (DDM) algorithm (De Bleser, 2007) was used to identify promoters which are highly and exclusively expressed in the heart and relatively enriched in a combination of cis-acting regulatory elements. In short, it can be expected that the responsiveness of the two sets of promoters of differentially regulated liver-specific genes to a given stimulus can be explained by transcription factor binding sites (TFBSs) shared by both sets of promoters, though this may not explain the direction of the response. Next to this common set of TFBSs, every set of promoters might bear one or more TFBSs that are more characteristic of the promoters of the up-regulated or of the down-regulated group of genes, and might explain, at least partially, the observed differential behavior. These "differential" TFBSs can be found using the following procedure. First, every promoter of each set is used as input for the MATCH™ program (Kel et al., 2003), or any other similar program, which will predict TFBSs on it using a precompiled library of positional weight matrices (PWMs). The results, being the number of predicted TFBSs per PWM per promoter (further referred to as counts), are collected in the form of a matrix in which each row corresponds to a promoter sequence while the columns correspond to the used PWM. The columns are further referred to as PWM-vectors, characterizing a PWM by its number of predicted TFBSs per promoter. The choice for using the total number of predicted TFBSs per PWM per promoter is motivated by the observation of Papatsenko et al. (Papatsenko et al., 2002) that regulatory regions of *Drosophila melanogaster* contain multiple copies of robust motifs as well as weaker copies. In general, it is reasonable to assume that the presence of multiple binding sites for a transcription factor plays an important role. Moreover, it was shown in yeast that genes whose promoters share pairs of TFBSs are significantly more likely to be co-expressed than genes whose promoters have only single TFBSs in common (Pilpel et al., 2001). In line with this observation, the mere combination of single liver-specific TFBSs to yield composite enhancer elements yielded disappointing results (Lemken et al., 2005). As the DDM method considers both overrepresentation and association, considering multiple matches per promoter may help discover putative functional TFBSs by overrepresentation. Two TFBSs are considered correlated if their corresponding columns in the matrix are similar. Similarity between the columns can be measured using a distance function. With this approach, distance matrices summarizing all TFBS associations are constructed for the TFBSs in both sets of promoters. Finally, by calculating the DDM and performing multidimensional scaling (MDS) on this matrix to visualize its content in two dimensions, we can distinguish TFBSs that do not contribute to the observed differential gene expression, as they will be mapped near the origin of the DDM-MDS plot, from "deviating" TFBSs that are likely responsible for the observed differential gene expression. As the MDS procedure will plot TFBSs that are strongly associated closer together than less associated ones, it highlights most of the otherwise often fuzzy interactions between TFBSs in the promoter datasets. Alternatively, results can be summarized in a table.

The rationale behind this procedure is based on association and individual overrepresentation (of one condition compared to the other). Indeed, although it is known that many transcription factors are specifically upregulated in the liver, this does not automatically imply that these are involved in upregulating gene expression in vivo. Important modules in one condition but not the other will be characterized by the overrepresentation of their consisting TFBSs and will be associated. This results in low DD values for two associated TFBSs, whereas the DD value for a TFBS that is overrepresented and common TFBSs will be high. Whether the TFBSs (and module) is typical for either the first or the second set of promoters can be derived from the sign of the column value sum of the original DDM.

The genomic context of upregulated genes was also taken into account, as described in PCT/EP2009/054724 and De Bleser et al., 2007. This involves searching binding sites conserved across multiple species, and for combinations of motifs rather than a single binding site; so that the likeliness that the identified sequences are actually involved in regulating gene expression increases. Indeed, it is well established that the mere presence or absence of transcription factor binding sites in a given promoter is not sufficient to confer high-level tissue specific expression. It is the combination of TFBSs as "regulons" within a particular chromosomal context that is key in dictating high-level tissue-specific expression. This approach led to the identification of 8 regulatory sequences enriched in the above transcription factor binding sites, summarized in Table 1.

These regulatory elements were highly conserved among evolutionary divergent species (suggesting strong selective pressure to maintain high-level expression). Eight regulons enriched in transcription factor binding sites (TFBS) and capable of dictating high-level heart-specific expression were identified. Computational approaches were used to discover and characterize these tissue-specific enhancer modules. No prior knowledge of the motifs they contain is needed. The approach consists of following subsequent steps: (1) identification of tissue-specific genes that are highly expressed based on statistical analysis of microarray expression data of normal tissues, (2) extraction of the corresponding promoter sequences from publicly available genomic databases and (3) identification of the regulatory modules and the motifs they contain, using a novel distance difference matrix (DDM) approach. With the DDM approach we can both detect enhancers and silencers and model them as sets of the motifs they contain. (4) Next we search the genomic context of the highly expressing tissue-specific genes for clusters of motifs that are part of these sets. If these clusters coincide with regions that are highly conserved within several species, these regions are considered as putative enhancer modules. These cis-acting regulons and their sizes are as shown in Table 1 below. These different regulons were synthesized with Acc65I flanking restriction sites at both ends (Table 1). These enable easy cloning of the regulon into the AAV vector. SEQ IDs 1-8 correspond to the regulatory sequences shown in italic, SEQ IDs 9-16 include the sequences with restriction sites.

TABLE 1

All the regulons were flanked by Acc65I restriction site (in red) to allow cloning into Acc65I cloning site in AAV vector. Regulatory sequences in italic, sequences used for cloning underlined. SEQ IDs and bp size between brackets refer to the enhancers with cloning sequences, the others to the enhancers as such.

| | Regulon | Size (bp) | Sequence |
|---|---|---|---|
| 1 | Myl3 SEQ ID NO 8 (16) | 123 (149) | GGCGCGCCACCTCATGACCCCAGCCCCACCCCTGCAGTGCACAA TAGGGACAGGGCCATAAAAGGATATGGCTAGGCTTAGGGGCTATTTTGG GGCCTGGGGAGGGCATTGTTCAGGCTCAGGAATGGGTAACGCGT |
| 2 | Brd7 SEQ ID NO 7 (15) | 662 (688) | GGCGCGCCTCCAGTCAGGCCCGCCTGAGATTACCTAGGTGTTCT GGTGACTTCTGAGGGCCTCGCATGAAAGATAACGCCCAAATCAACAAAT CTGCCATTGTGGCTTTGAAGAGACTGTTTCAATCACTTTATTTTGTCTTTAT GTCAGGTTTGCCAGATGGCTTGGGTCTTTCTGAGGTCCTGTACCGAGGG GGCACAGAGAGAACTGGTGCAGCTTCAAAGCTCCTTTTTAATCTTTAGCA ACATCACAGCGGCTGGGAAACTGCCTCGGCTCCCTCAAGTCTCTCCCACA AAAGAGGCGCGGCCGAGGCTCTAATGAAAGCCAGATAAAGGGATGGCT GGAATCAGAAACAGAGGGAAAAGAGCAGTCGTTAGTCTTTCTTGTAGCT GTTTCAAAAGAAATTCTAAGACAAATTATGGCTTTGGGTGTTTTTCTAAA AGGACTGCAGCAGGGAGAGGAGGTGGGGGAGGTGCTTTGACCCCTCAG CACCCTTCCCCTTGCATGAAAGGCAGAGGAGACTGAAAAAAGGCTGAAA TACAACAATAAACTTTCTGCTTGTGCGCGTGGGGATGAAAGGCGCGCTG GCATAATTATGGGCGAGGGTGCGCGGGGCGGGCGGGCGGCTTTACCT TGCCGCCAGCGCTATTAATGATGAGGCTCCCTCTTACGCGT |
| 3 | Myl2 SEQ ID NO 2 (10) | 156 (182) | GGCGCGCCCCAGCTCTCTGCAGCCCAGGAACAATAAATACTTCC TCCCCATGTTTAAAAATAACCCCATGACCGCTTTTGGCAGTCATAGGTGA GGCGGGCACCACCTAAGGCCCCCCC4ACCCCATGCCGTTCTTCTGAAGTA AGGGTGGCTCACTCGCCACTGACGCG |

TABLE 1-continued

All the regulons were flanked by Acc65I restriction site (in red) to allow cloning into Acc65I cloning site in AAV vector. Regulatory sequences in italic, sequences used for cloning underlined. SEQ IDs and bp size between brackets refer to the enhancers with cloning sequences, the others to the enhancers as such.

| | Regulon | Size (bp) | Sequence |
|---|---|---|---|
| 4 | Casq2e1 SEQ ID NO 1 (9) | 192 (218) | GGCGCGCCAGTAGAAAAACAGCCAAGCTAGGGAGGCTGGGAG GCCAAGCCCCAGATACCTTACATAGCTCTGCTCAGCCTCTGTCTCATTAGG AACTCCATTTTTAGGATGCAGTTGTTTCAGGCTAAAAATAAATCATGCAA TGAATAAAAAAGTTAGATACGACACTGTAGAGGGATTCGCTGATACAGT CTGTCCGAACGCGT |
| 5 | Casq2e2 SEQ ID NO 3 (11) | 90 (116) | GGCGCGCCATTATTCTTTTTTTACAAAGCGTTTTCTTTCCTTATTA TTTATTTTTGCTTGGGCTAATTTTAAAATGAGTTTTTATTCCCTTGGTACAA ACGCGT |
| 6 | Ankrd1e1 SEQ ID NO 4 (12) | 272 (298) | GGCGCGCCTGAATCAGGAAGAAATGTGAGAGGGCCATTCCTTT GGTGGTGATCACATCGCTCAGCAATGCAAGTCATCCTATTTGTCAAGAGT CAGGGGACAGCTGTCTGTTGACATTGCACCACATCACTGCCCTTTTTTCT TTGTCAGCTTTCATATGACTACCTATCAAGAAAATGTAGATGCCCTACATA TCACACCCCCAGTAATATCTTTCTGATAAGCAGACTTATCAACACTTCACT TAGGGGAAACTTGTCCCAGGACATCCTATTCCCTACGCGT |
| 7 | Ankrd1e2 SEQ ID NO 5 (13) | 250 (276) | GGCGCGCCGATTGTCATAGTAACGCTCTGAAAAGATTTTGATG CAACTTTGGAATTACTTCACACCCAATTACATAGAACATCTACTTGGAATG AGAGATAAGTGCTTCTGTGACTGCAAACATAGATAGAAAATCCATTAACC TTTTTAGCCATTTATTAAAGCAGAGGAAAATTATTTTTAAAATGCAATTTC TGACTTCAAGAAGAAGTACCGAAAAAAATATTTTCTTGGTGTAGTTTGGA GTTTCCTAATAAAACGCGT |
| 8 | Ankrd1e3 SEQ ID NO 6 (14) | 370 (396) | GGCGCGCCAAGATGATGTCCTTCCTTATTTGGTGGCTCTGGAA GCCACATTCCCTCCTCATCCGCCTTCCCAAAAGAACCTTGTGGCTGCCCAG CGGAAGCCAGTGCTTTCAGCAGCCCCCACCCTTGGCATTTCCTTATCTAGG AGTCTTCACTGTGGAATTCCAAGGCCCACCCCAATGCTCCGGATGTGTTT CAATCCATGGCCTGCCACTTTGTTACTCTTGTGATGACAAGCAGATAACAT AGCTCACATGCCTTCTTTTCCTGCATACCAACCAGACCCCAGTTCTGAAAA GGAAACAAACCACAAACCAAGAGAGATGTGTTATTTTTATGCAGACATT GTTAAGACACTGCAATAAGCCTAGAATTGTGGACGCGT |

Amplification of Fragments to Generate Vectors

All PCR involved in this study were carried out with Accuprime PCR reaction kit (Invitrogen) based on pfx DNA polymerase enzyme with 30 cycles of amplification.

Amplification of Mouse Alpha Myosin Heavy Chain (αMHC) Promoter

The alpha-myosin heavy chain (αMHC) promoter was selected for this project because it has been shown to confer global and very high level of cardiac specific expression of transgene among other heart specific promoters (Pacak et al., 2008).

The αMHC promoter was amplified from a mouse genome obtained from the liver of a mouse provided by our lab. The primers were ordered from Invitrogen and designed with reference to the sequence from the link provided by Pacak et al., that is, Catalogue of Regulatory Elements (worldwide web cbil.upenn.edu/MTIR/TOC.html). The primers used are shown below.

Forward primer (44 bases) with Acc65I restriction site: 5' to 3'-ATA GGT ACC GGT GAC CCT TAC CCA GTT GTT CAA CTC ACC CTT CA (SEQ ID NO:20) and reverse primer (33bases) with NheI restriction site: 5' to 3'-ATA GCT AGC GGG TTG GAG AAA TCT CTG ACA GCT (SEQ ID NO:21)

Amplification of Humanized Recombinant Green Fluorescent Protein (hrGFP)

Using standard conditions, the hrGFP was amplified from a plasmid construct, pAAV-hrGFP from Stratagene using primers obtained from Invitrogen. The primers used were obtained from Invitrogen and are listed below. Two restriction sites, NheI and BglII were incorporated in the primers to flank the amplified fragments (forward primer (40 bases) with NheI restriction site: 5' to 3'-TTG CTA GCA CCA TGG TGA GCA AGC AGA TCC TGA AGA ACA C (SEQ ID NO:22); reverse primer (36 bases) with BglII restriction site: 5' to 3'-TTA AGA TCT TTA CAC CCA CTC GTG CAG GCT GCC CAG (SEQ ID NO:23)).

Amplification of Beta Globin Intron (β-Globin Intron)

Beta globin intron (β-globin intron) was amplified from a Stratagene plasmid construct (pAAV-hrGFP) using primers obtained from Invitrogen. This amplification was carried out following the same standard procedures as the other constructs. The primers used are as below.

Forward primer (25bases) with XbaI restriction site: 5' to 3'-ATA TCT AGA ATC CCG GCC GGG AAC G (SEQ ID NO:24). Reverse primer (36 bases) with NheI restriction site: 5' to 3'-ATA GCT AGC AAT CGA TGT TCG AAT CCC AAT TCT TTG (SEQ ID NO:25).

Purification and Restriction of Amplified Fragments

The resulting amplified αMHC, hrGFP and β-globin intron fragments were purified using spin columns according to Qiagen gel extraction kit. After elution, the αMHC was digested with Acc65I and NheI restriction enzymes, the hrGFP was digested with NheI and BglII restriction enzymes, and β-globin intron was digested with XbaI and NheI restriction enzymes. The digestions were aimed to generate sticky ends of the fragments to enable ligation into vector. The fragments were then purified with spin columns as in Qiagen gel extraction assay kit. The fragments were kept in −20° C. freezer until needed.

Cloning of Heart-Specific Regulons into AAV Vector Containing αMHCp-β-Globin Intron-hrGFP-pA Generation of the construct (pAAV-αMHCp-β-globin intron-hrGFP-pA) (FIG. 4 [C]) involved 4 sub-clonings which are described below. Once this vector was cloned and confirmed by sequencing, the eight identified regulons were subsequently cloned into this generic AAV construct.

Generating the Backbone of the Vectors

Figure 4:
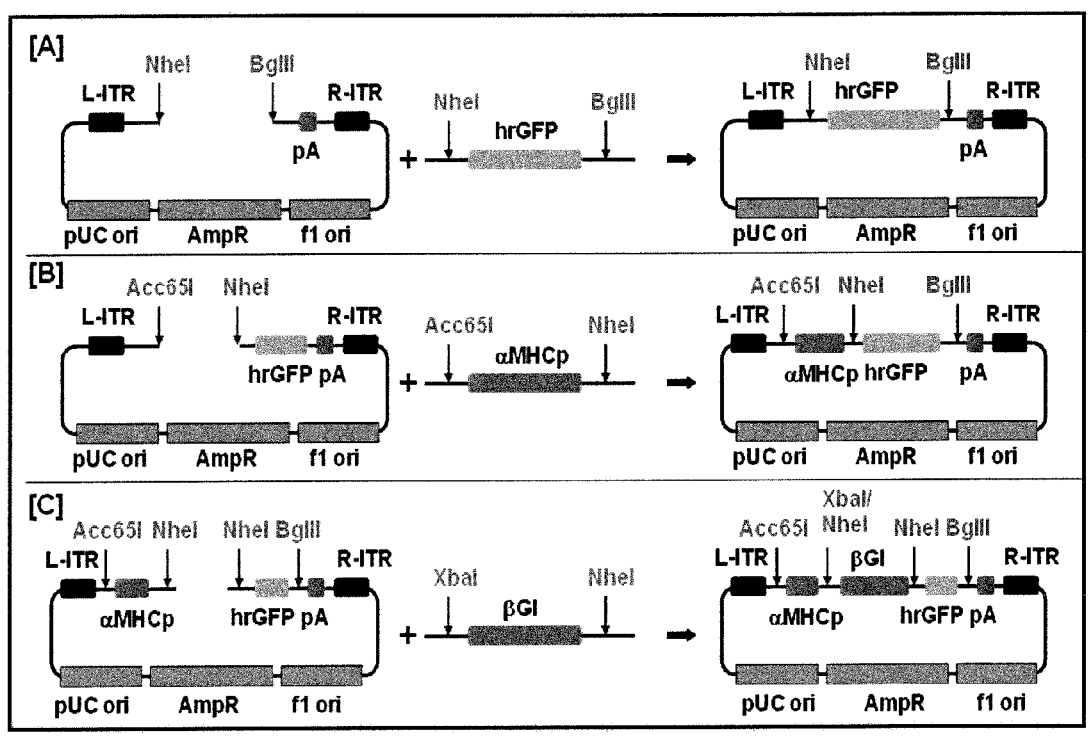
FIG. 4. Generation of pAAV-αMHCp-βGI-hrGFP-pA. The first vector fragment was generated using NheI and BglII restriction enzyme digestion to make ligation possible with the amplified hrGFP insert, which was flanked by NheI and BglII restriction sites to yield pAAV-hrGFP-pA [A]. The pAAV-hrGFP-pA vector was then digested with Acc65I and NheI restriction enzymes and was ligated with αMHCp flanked by Acc65I-NheI sites. This yielded pAAV-αMHCp-hrGFP-pA [B], which in turn was digested with NheI restriction enzyme. The resulting vector plasmid after ligation with beta globin intron (βGI) was pAAV-αMHCp-βGI-hrGFP-pA [C].

The backbone of the plasmid construct used in this research contained an ampicillin selection marker gene, L- and R-ITR segments of AAV2 viral gene and a bovine growth hormone polyadenylation (polyA) cDNA (FIG. 4[A]). This plasmid backbone was generated from a plasmid construct, pAAV-TTRserp-FIXIA-pA, from our lab. By three characteristic restriction sites (BglII, NheI and XbaI) in the plasmid, the fragment was generated with three restriction enzymes BglII, NheI and XbaI. The BglII restriction site was located immediate downstream of the pA, NheI site was adjacent and also downstream of the L-ITR site and the XbaI site was located midway between the BglII and the NheI sites. These sites were used because it could allow easy separation of the generated backbone bigger fragment flanked by BglII and NheI sticky ends, from the other two smaller fragments where one fragment is flanked by NheI and XbaI and the other by XbaI and BglII sticky ends of the respective restriction sites.

The band corresponding to the size of the fragment of interest was separated from the rest of the reaction mixture using gel electrophoresis on 1% agarose gel. The fragment was then purified from the gel following the protocol accompanying Qiagen plasmid gel extraction kit. The purified fragment was stored at −20° C. freezer until needed.

Cloning the hrGFP

The hrGFP and the backbone of the vector which includes the ITRs, selectable marker gene and a pA were ligated together. This was possible because both the hrGFP and the backbone had NheI and BglII restricted sticky ends, which could mediate the ligation of the ends. After an overnight incubation of the ligation reaction, the newly generated construct, pAAV-hrGFP-pA was used to transform XL-10 Gold ultra-competent bacteria cells from Stratagene, plated on an LB Agar solid medium with ampicillin and incubated overnight. Plasmid DNA was extracted from 20 colonies using Miniprep assay kit from Invitrogen. The DNA obtained was then screened for positive clones using BglII-NheI restriction enzymes.

Cloning of pAAV-αMHCp-hrGFP-pA

The pAAV-hrGFP-pA plasmid construct was first restricted with Acc65I and NheI restriction enzymes, which create two sticky ends upstream of the hrGFP. The α-MHCp which had been restricted with these two restriction enzymes, as mentioned above, was then ligated with the opened pAAV-hrGFP-pA flanked by the sticky ends of Acc65I and NheI restriction sites. The resulting plasmid, pAAV-αMHCp-hrGFP-pA was then transformed into XL-10 Gold ultra-competent bacteria cells. Positive clones were screened using Acc65I-NheI restriction which removes the αMHCp from the rest of the construct revealing a band of 363 bp corresponding to the size of the α-MHCp. A further confirmatory test using NotI-Nde together in a restriction was carried out, which cut out a 329 bp fragment of the αMHCp since the NdeI is located inside the promoter region.

Cloning of pAAV-αMHCp-β-Globin Intron-hrGFP-pA

To obtain this clone, the pAAV-αMHCp-hrGFP-pA selected clone was digested with NheI restriction enzyme to create a single restriction at the NheI site located between the αMHCp and the hrGFP genes (FIG. 4[C]). During the restriction reaction, phosphatase was added to the restriction reaction to remove the 5'-phosphate groups from the restricted fragments. This was done to prevent re-ligation of the opened plasmid vector. The fragment was then purified using Qiagen plasmid gel extraction kit.

Gel electrophoresis was carried out whereby the vector fragment pAAV-αMHCp-hrGFP-pA (opened) was run side-by-side with the insert, β-globin intron to determine the relative concentration of both. This was to enable the estimation of the right volumes to take from each fragment for the ligation reaction since the standard ligation reaction requires a 3:1 insert to vector concentration ratio.

After estimating the volumes of each of the fragments to be used, the ligation reaction was made and incubated at room temperature to allow efficient ligation of the vector and the insert. The resulting mixture was used to transform XL-10 Gold Ultra-competent bacteria cells and cultured overnight in LB-ampicillin solid medium. Colonies obtained were screened for positive clones using NheI-Acc65I in one restriction reaction. The selected positive clones were further confirmed using three other sets of restrictions involving NdeI-NheI, NotI-NheI, BglII-NdeI as well as NheI-Acc65I restriction reactions. It must be noted that the NheI site upstream of the β-globin intron was destroyed due to the ligation reaction which ligated a NheI site with XbaI site. This means that only one active NheI site remained after the ligation reaction located downstream of β-globin intron. NdeI restriction site was located in the αMHCp, NotI site was located immediate downstream of the L-ITR before the Acc65I site, which was upstream the promoter site whilst BglII was downstream the hrGFP gene.

Production of pAAV-αMHCp-βGI-hrGFP-pA Plasmid Vector

A selected and confirmed positive clone of the pAAV-αMHCp-βGI-hrGFP-pA plasmid was used for transformation in XL 10-Gold Ultra-competent bacteria cells. After an overnight incubation, a pre-culture was made from a careful picking of only one colony into a 2 ml LB-ampicillin liquid medium in a culturing tube. The culture was subjected to 150 rpm, 37° C. incubation. The culture was used to inoculate a culturing flask of 2 liter (L) LB-ampicillin medium. This flask was incubated for about 13 hours (left overnight) by shaking in 37° C. and 150 rpm incubator but until the bacteria growth reached an optical density (OD) between 1.6-1.9 at a 280 nm absorbance. At this OD, the plasmid DNA was extracted using Maxiprep assay kit from Invitrogen. After ethanol precipitation and purification, the concentration of the pure plasmid was determined using Nanodrop ND-1000 spectrophotometer (Nanodrop Technologies, Rockland, Del., USA) and the concentration adjusted to 1.0 μg/μl. Purified plasmids were stored at −20° C. until needed for AAV vector production. Results obtained from control sequencing revealed the vector, pAAV-αMHCp-βGI-hrGFP-pA contains all the cloned fragments and in their right orientation, that is, sense orientation.

Cloning of the Regulons into pAAV-αMHCp-βGI-hrGFP-pA Plasmid Vector

Figure 6:
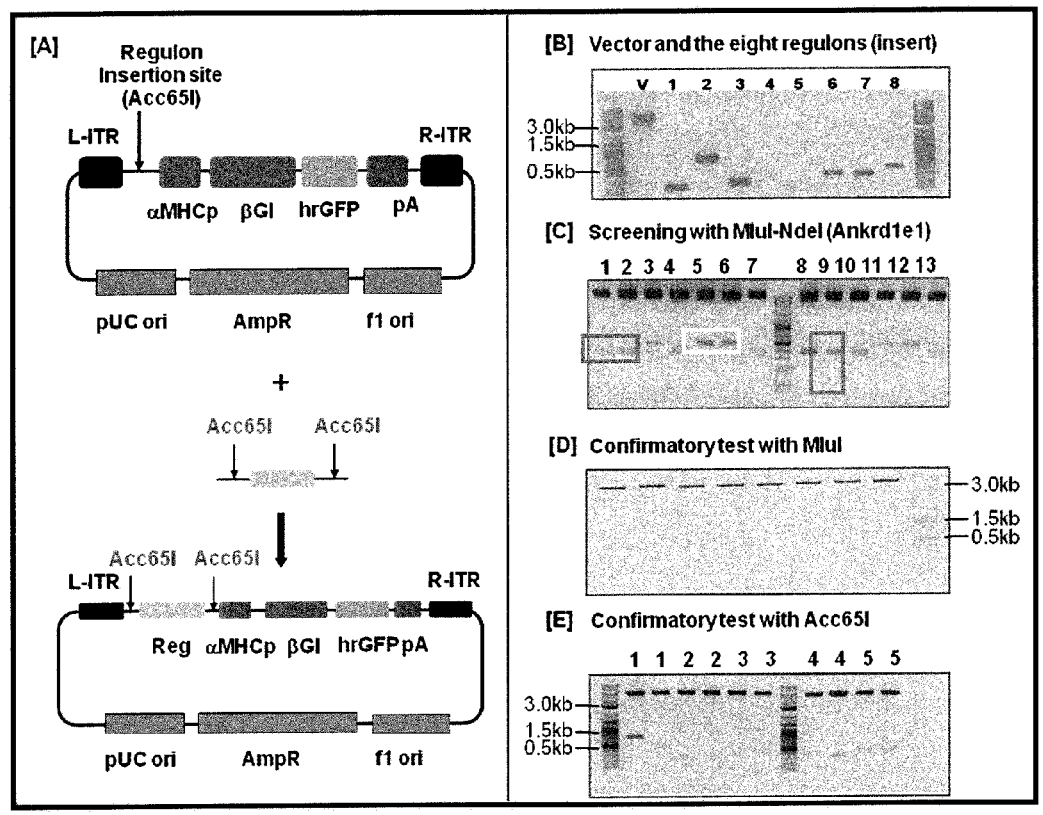
FIG. 6. Generation of pAAV-Reg-αMHCp-βGI-hrGFP-pA. Each regulon was flanked by Acc65I restriction sites on both sides and cloned after the pAAV-αMHCp-βGI-hrGFP-pA vector was digested with Acc65I restriction enzyme. The enzyme cuts the Acc65I site located downstream of the L-ITR, thus, each of the eight expression cassettes resulting from cloning the eight regulons had its regulon between the L-ITR and the αMHCp regions [A]. [B] Electrophoregram showing all the eight regulons (well numbers 1-8) before cloning into the vector (V=pAAV-αMHCp-(GI-hrGFP-pA) after treatment with Acc65I and phosphatase. [C] MluI-NdeI restriction was used to determine the vector clone with the regulon in the sense or antisense orientation. Red box=bands of sense fragments, yellow box=bands of fragments in antisense orientation, blue box=bands resulting from the presence of an NdeI site in the regulon. [D] After treatment of MluI, all the clones showed only a single band and means none of the clone had the regulon in tandem [E]. To confirm the right regulon in selected positive clones, Acc65I restriction was carried out (1-5→vectors with regulons treated: 1=Brd7; 2=Casq2e1, 3=Ankrd1e1, 4=Ankrd1e2, and 5=Ankrd1e3). The same standard dye was used for all ladders and it was TryDye 2 Log from Westburg.

All eight regulons that had been synthesized: Myl3, Brd7, Myl2, Casq2e1, Casq2e2, Ankrd1e1, Ankrd1e2, and Ankrd1e3, were cloned into the vector yielding a total of eight different expression cassettes and resulting in new constructs designated as pAAV-Reg-αMHCp-βGI-hrGFP-pA (FIG. 6[A], Reg=position of regulon). The regulons were cloned upstream of the αMHCp.

Each of the eight regulon constructs were screened for positive clones and further confirmed with other restriction enzymes before being used for large scale plasmid extraction for the viral vector production.

Plasmid Production

This production involved the expansion of one selected positive clone per regulon. The plasmids were used to transform and culture XL-10 Gold ultra-competent bacteria cells. After an overnight incubation, pre-culture were made from a careful picking of single colonies into 2 ml LB-ampicillin liquid medium in a culturing tube. The cultures were then subjected to 150 rpm, 37° C. incubation and were used to inoculate culturing flasks of 2 liter (L) LB-ampicillin medium. These flasks were incubated for about 13 house (usually overnight), by shaking in 37° C. and 150 rpm incubator but until the bacteria growth reach an optical density (OD) between 1.6-1.9 at a 280 nm absorbance. At this OD, the plasmid DNA were extracted using Maxiprep assay kit from Invitrogen to obtain very pure plasmid vector, which were stored in −20° C. until ready for transfection. Each purified plasmid was reconfirmed with restrictions using KpnI, MluI, MluI-NheI, MluI-NdeI restriction enzymes before used for AAV production.

AAV Production

Calcium Phosphate Transfection

Specialized AAV producing cell line called 293 cells supplied by Stratagene were used for the calcium phosphate transfection. This transfection was a three plasmid component system involving three plasmids, the AAV vector produced (section 3.3.5), AAV9 rep/cap helper genes in a plasmid construct, and adenovirus helper genes obtained from Stratagene. With the addition of calcium chloride ($CaCl_2$) and a phosphate supplied by the Hepes Buffered Saline (HBS) from kit, the DNAs including 104 μg of adenovirus helper genes, and 50 μg each of AAV vector and AAV9 rep/cap helper genes were precipitated and via calcium phosphate transfection, were taken up by prepared HEK 293 cells.

In preparation for the transfection, a master stock of 293 cells was seeded and cultured until 70% confluent in 75 $cm^2$ flask. It was split into 3 flasks and allowed to grow until 70% and subsequently split into trays. This process of splitting and growing were repeated until desired amount of cells were obtained. The cells were then kept frozen in aliquots of 25% and thus, served as the working stock for the whole production. Before each round of transfection, a working stock were obtained, split and allowed to grow into a confluence of 50% before used for the transfection. All transfection were carried out according to a protocol accompanying the calcium phosphate transfection kit by Invitrogen. A GFP driven by CMV promoter in AAV vector plasmid was always used as control for each round of transfection.

The cells were harvested 48 hours post transfection. The procedure involved scraping the cells from the cultured plate and collecting into centrifuge bottle on ice. At a speed of 3400 rpm and a temperature of 4° C., the cells were collected from the culturing medium after 15 minutes of centrifugation and discarding the supernatant. The cells were then stored with 10 ml AAV buffer immediately at −80° C. awaiting purification.

AAV Viral Purification

Since AAV does not lyse its host cell, the viral particles were rescued from their host cells through a process of freezing and thawing of the cells followed by sonication. The released viral particles in the cell lysate were then purified through a three times (3×) cesium chloride (CsCl) gradient centrifugation between 18 to 20 hours in ultracentrifuge. In setting up the CsCl gradient, first, a mix of 0.454 g CsCl/ml cell lysate were made, followed by subsequent addition of different gradient of CsCl solution including 1.31 g/ml CsCl, 1.41 g/ml CsCl, and 1.61 g/ml CsCl. Using Abbe refractometer, the refractive indices (RI) of fractions from spin were measured and those that had RI between 1.3650-1.3760 were pulled together for subsequent rounds of spin. The final resulting pure vector suspension were then stored at 4° C.

AAV Viral Vector Titration

4 μl of the purified rAAV vector suspension was first treated with DNase and incubated at 99° C. for 5 minutes. This step was necessary to destroy any vector DNA that resided outside the AAV9 viral particles including any remaining DNA used for transfection or from the genome of the cells used for the transfection. This means that only DNA inside the viral particles would be titrated during the real-time or quantitative polymerase chain reaction (QPCR). This temperature also allows rupturing of the viral particles to release their vector DNA into solution.

The QPCR was performed in ABI7500 FAST (Sequencer Detector Unit from Applied Biosystems, Foster, Calif., USA) using ABI (PERKIM ELMER) Q-PCR master mix and TAQMAN probe and primers specific to detect bovine growth hormone polyA (BGH pA) as transgene DNA target sequence. Specific Standards were prepared (dilution $10^8$-$10^2$) to get a standard curve which enabled determination of signal on each sample. Based on the size of the plasmid and Avogadro's number, the μg of plasmid DNA could be correlated to a specific copy number of the target DNA.

To detect the polyA, specific primers which were forward and reverse primers, with probe were used. The forward and reverse primers used were GCCTTCTAGCCAGCCAT (SEQ ID NO:26) and GGCACCTTCCAGGGTCAAG (SEQ ID NO:27) respectively. The probe used was TGTTTGC-CCCTCCCCCGTGC (FAM-TAMRA) (SEQ ID NO:28). A reaction mix containing ABI QPCR reaction Mix, primers, probe, ROX and water to top up to required volume was put in each reaction well. After loading the samples, standard and the non-template control (water) onto the 96 well QPCR plate, the QPCR was run from ABI7500 standard running: 50° C. for 10 minutes, 95° C. for 2 minutes and subsequent 40 cycles of 95° C. for 15 seconds and 60° C. for 1 minute making each run last for about 1 hour and 35 minutes.

In Vivo Experiments

Injection of AAV9 Viral Vectors

A total of eleven 23 days old NOD-SCID$\gamma_c$ null mice were injected intravenously via tail vein injection with specific recombinant (r) AAV9 as summarized in Table 2. The viral vectors were diluted in phosphate buffered saline (PBS) with injection dose of $1.25 \times 10^{11}$ vg (vector genome).

TABLE 2 rAAV9 vectors used to test in vivo GFP expression from 23 days old NOD-SCID$\gamma_c$ null mice

| rAAV9 vector | Number of mice | Dose and volume per mouse |
| --- | --- | --- |
| rAAV9-αMHCp-βGI-hrGFP-pA | 4 | $1.25 \times 10^{11}$ vg in 42 μl + 158 μl PBS |
| pAAV-Myl2-αMHCp-βGI-hrGFP-pA | 4 | $1.25 \times 10^{11}$ vg in 170 μl + 30 μl PBS |

TABLE 2-continued rAAV9 vectors used to test in vivo GFP expression
from 23 days old NOD-SCID$\gamma_c$ null mice

| rAAV9 vector | Number of mice | Dose and volume per mouse |
|---|---|---|
| pAAV-Casq2e1-αMHCp-βGI-hrGFP-pA | 3 | $1.25 \times 10^{11}$ vg in 200 μl |

Reverse Transcriptase-Polymerase Chain Reaction (RT-PCR)

Semi-quantitative RT-PCR was used to detect mRNA abundance for hrGFP in the tissues from all the mice. Total RNA was extracted from the heart and spleen tissues of mice following protocol accompanying Invitrogen PureLink Micro-To-Midi Total RNA Purification System kit. DNAse treatment step was included to degrade genomic DNA or the vector DNA. This was followed by cDNA synthesis with 2 μg of total RNA using Invitrogen SuperScript VILO cDNA Synthesis kit and the protocol that accompanies it. 100 ng of total cDNA was used to carry out PCR in order to detect the level of hrGFP in the cDNA. This was performed using hrGFP specific primers, the same as mentioned above. (Forward primer: 5' to 3'-TTG CTA GCA CCA TGG TGA GCA AGC AGA TCC TGA AGA ACA C (SEQ ID NO:22) and reverse primer: 5' to 3'-TTA AGA TCT TTA CAC CCA CTC GTG CAG GCT GCC CAG (SEQ ID NO:23)). Amplification was performed in a thermal cycler. Glyceraldehyde-3-phosphate dehydrogenase (GAPDH) cDNA served as the internal control gene for normalization of the sample loading. The primers used for the GAPDH were TGTGTCCGTCGTG-GATCTGA (SEQ ID NO:29) as forward primer and CCTGCTTCACCACCTTCTTGA (SEQ ID NO:30) as the reverse primer. The plasmids used for standards were pAVV-hrGFP for hrGFP and the pGEMT easy-mouseGAPDH plasmids for GAPDH.

Example 1

Generation of Hyperactive Cardiac Specific Regulons by Distance Difference Matrix (DDM) Approach It is known that the particular combination of transcription factor binding sites (TFBS), defined as "regulon," is key in dictating high-level tissue-specific expression, not just the mere presence of the TFBS. Using novel data mining algorithm based on DDM, eight cardiac-specific regulons highly enriched in TFBS were identified and the respective sequence were presented in Table 1. The principle of the DDM method can be illustrated by example of the mapping of the MYL3 enhancer on the human genome. As the gene myosin light chain 3 is specifically expressed in the heart, its enhancer region contains several heart-specific transcription factor binding sites (TFBS), such as Sox5, Pax4, RREB1 and others. Furthermore, these TFBS are highly conserved within several species indicating that binding of the corresponding transcription factors to these DNA binding sites is under strong evolutionary pressure. When mutations occur that alter such interaction, the resulting change in gene expression can be incompatible with survival. The eight regulons that were identified by this DDM approach namely: Myl2, Brd7, Myl3, Casq2e1, Casq2e2, Ankrd1e1, Ankrd1e2, and Ankrd1e3 illustrated strong homology among different species, such as rhesus, mouse, armadillo, dog, horse, lizard, chicken, among others.

MYL3 (Refseq: NM_000258) encodes myosin light chain 3, an alkali light chain also referred to in the literature as both the ventricular isoform and the slow skeletal muscle isoform. Mutations in MYL3 have been identified as a cause of mid-left ventricular chamber type hypertrophic cardiomyopathy.

The protein encoded by the Ankrd1 gene (Refseq: NM_014391) is localized to the nucleus of endothelial cells and is induced by IL-1 and TNF-alpha stimulation. Studies in rat cardiomyocytes suggest that this gene functions as a transcription factor. Interactions between this protein and the sarcomeric proteins myopalladin and titin suggest that it may also be involved in the myofibrillar stretch-sensor system.

The protein encoded by the CASQ2 gene (Refseq: NM_001232) specifies the cardiac muscle family member of the calsequestrin family. Calsequestrin is localized to the sarcoplasmic reticulum in cardiac and slow skeletal muscle cells. The protein is a calcium binding protein that stores calcium for muscle function.

MYL2 (Refseq: NM_000432) encodes the regulatory light chain associated with cardiac myosin beta (or slow) heavy chain. Ca+ triggers the phosphorylation of regulatory light chain that in turn triggers contraction. Mutations in MYL2 are associated with mid-left ventricular chamber type hypertrophic cardiomyopathy.

Figure 3:
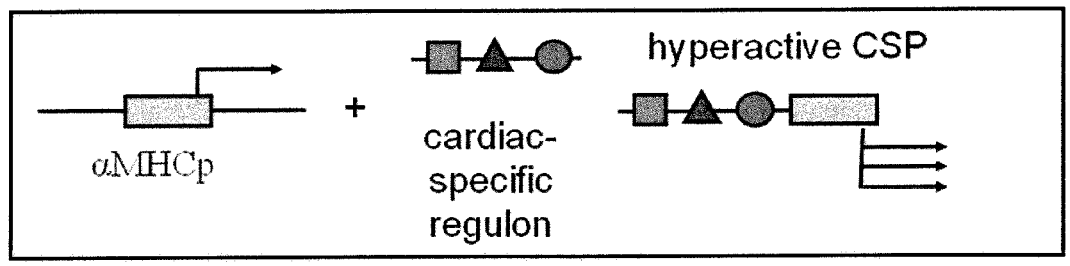
FIG. 3. Hyperactive cardiac-specific promoter resulting from the combination of αMHCp and cardiac specific regulons highly enriched with TFBS to enhance hyperactivity. Expression cassettes were then generated from each regulon using the αMHCp. A total of eight expression cassettes were therefore generated through cloning.

It was then hypothesized that a combination of a potent heart-specific promoter and heart-specific regulons enriched with TFBS would dictate hyperactive heart-specific expression. The αMHCp in combination with these cardiac-specific regulons was hypothesized to yield hyperactive cardiac-specific promoter (CSP) to dictate robust expression in the heart as shown in FIG. 3. These were then used to generate expression cassettes in AAV vector to test their robustness.

Generation of pAAV-αMHCp-βGI-hrGFP-pA

Recent advances in the use of AAV for gene therapy regarding its safety profile and its improvement in myocardial gene transfer (Vandendriessche et al., 2007; Müller et al., 2006) was the reason that AAV vector was chosen for this project to target the heart. In the generation of the AAV expression cassette used in this research, recombinant AAV was made by pseudotyping AAV2 into AAV9 capsid. This was in line with the fact that AAV9 has a highest tropism for the heart compared to other serotypes (Inagaki et al., 2006) and rAAV2/9-mediated gene delivery resulted in robust cardiac gene delivery (Pacak et al., 2008). To increase the specificity of the vector plasmid, alpha myosin heavy chain promoter, αMHCp, was incorporated into the cassette to drive the expression of the hrGFP transgene. Beta globin intron (β-globin intron) was also included to direct high-level expression of the hrGFP transgene (Buzina et al., 2008).

Generation of pAAV-hrGFP-pA

The pAAV-hrGFP-pA was obtained by ligating a pUC vector containing ampicillin resistant gene and the bgh-polyA with hrGFP fragment (FIG. 4[A]). After screening, the best clone was selected using NheI and BglII, which were the restriction sites at which the ligation was done. As observed on the electrophoretic image in FIG. 5 [A] this restriction produced a 716 bp fragment size, which was the size of the hrGFP. This was expected since NheI-BglII restriction would cut out the hrGFP fragment from the vector. This was a proof that the pAAV-hrGFP-pA selected vector contained the correct insert of the hrGFP fragment so further cloning could be subsequently performed using this vector.

Generation of pAAV-αMHCp-hrGFP-pA

Figure 5:
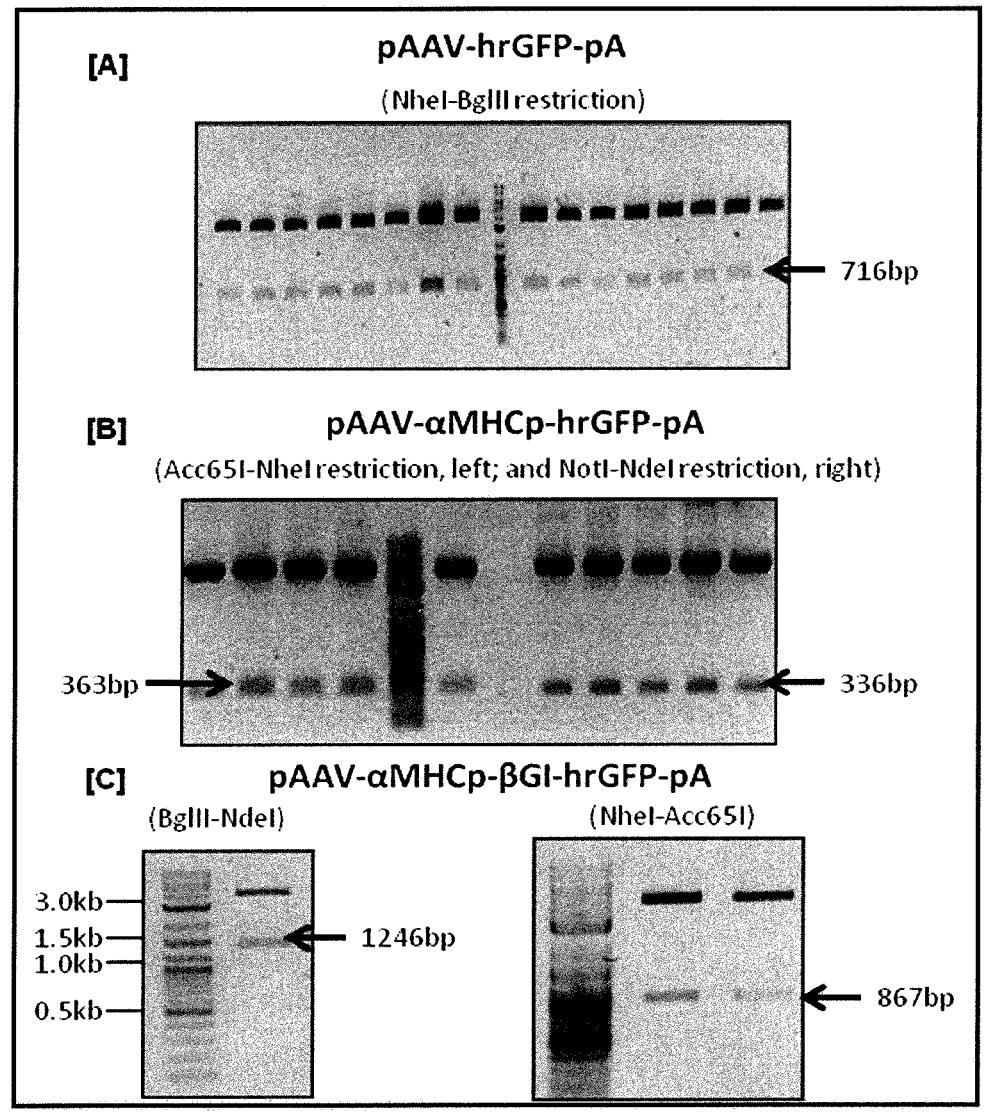
FIG. 5. Electrophoretic images for confirmatory restrictions in the generation of pAAV-αMHCp-βGI-hrGFP-pA. The clone obtained after hrGFP ligation into the pAAV vector was confirmed with NheI together with BglII restriction enzymes in one reaction. This restriction cut out the hrGFP fragment of 716 bp from the vector [A]. Likewise, the pAAV-αMHCp-hrGFP-pA was confirmed with Acc65I in a reaction with NheI to cut out the αMHCp of fragment length 363 bp. A further confirmation with NotI-NdeI restriction brought out 336 bp part of the αMHCp [B]. A confirmatory restriction with BglII-NdeI yields a 1246 bp fragment whilst NheI-Acc65I yields 867 bp fragments to confirm the presence of βGI in the vector construct [C]. Standard dye used for all ladder was TryDye 2 Log from Westburg.

The next step was to clone the alpha myosin heavy chain promoter (αMHCp) into the selected pAAV-hrGFP-pA positive clone. By utilizing the Acc65I and NheI restriction sites present in both the vectors and the amplified αMHCp, the pAAV-αMHCp-hrGFP-pA vector was obtained (FIG. 4 [B]). The correctness of this vector was confirmed with Acc65I-NheI and a fragment size of 363 bp was obtained corresponding to the size of the αMHCp (FIG. 5[B] left of ladder). A further confirmatory test resulting in cutting a 329 bp part of the promoter was carried out using NotI-NdeI restriction (FIG. 5[B] last five wells right of ladder). This was to test the presence as well as the efficacy of the promoter amplification from the mouse genome since the NdeI restriction site was located inside the promoter region about 20 bp to the end of the promoter sequence. This 20 bp less of the complete promoter region explains the lower bands produced with NotI-NdeI restriction as compared to the bands produced from Acc65I-NheI restriction (FIG. 5[B]).

Generation of pAAV-αMHCp-βGI-hrGFP-pA

The final construct before cloning of the regulons was to clone the beta globin intron (β-globin intron) into the pAAV-αMHCp-hrGFP-pA vector to yield pAAV-αMHCp-βGI-hrGFP-pA. As shown in FIG. 4[C], the preceding vector, that is, pAAV-αMHCp-hrGFP-pA was digested with NheI restriction enzyme to obtain a single cut in between the promoter and the hrGFP regions of the vector. In order to prevent vector re-ligation, this restriction reaction was treated with phosphatase, which removes phosphate groups from the 5'-end of the restricted fragment. Although the β-globin intron fragment had one end flanked by XbaI site, it could successfully be cloned into the vector, which was cut with NheI restriction enzyme. This is because both NheI and XbaI endonucleases produce a 5'-CTAG overhang after restriction even though each has a different recognition sequence—5'-TCTAGA for XbaI and 5'-GCTAGC for NheI—making ligation possible among fragments generated by these endonucleases.

Meanwhile, no confirmatory restriction could be carried out to cut out the β-globin intron from the vector because the NheI/XbaI site created in between the promoter and the intron after the ligation could neither be recognized by NheI nor XbaI. Hence, alternative restriction was done using BglII-NdeI and NheI-Acc65I digestion. As obtained in the electrophoretic image in FIG. 5[C], digestion of the pAAV-αMHCp-βGI-hrGFP-pA vector with BglII-NdeI restriction enzymes resulted in a band of 1246 bp signifying the presence of hrGFP (716 bp), the now cloned β-globin intron (492 bp) and 20 bp distal part of αMHCp, and two intervening restriction sites between the αMHCp-βGI, and βGI-hrGFP. The subsequent confirmatory test was to test the orientation of the inserted β-globin intron if in the sense orientation. In using Acc65I-NheI, it was expected that a vector with the intron in the sense orientation would generate a band of about 867 bp constituting the β-globin intron and the αMHCp with one intervening restriction site, NheI/XbaI site, which was exactly what was observed in the electropherogram shown in FIG. 5[C], right panel. On the other hand, a vector with the intron in the antisense orientation would have generated a 363 bp band of the αMHCp alone because in that case the destroyed NheI/XbaI would be residing in-between the β-globin intron and the hrGFP instead of between the β-globin intron and the αMHCp observed in the vector with the intron in the sense orientation.

Sequencing of pAAV-αMHCp-βGI-hrGFP-pA

All cloning and screening to obtain pAAV-αMHCp-βGI-hrGFP-pA were considered successful based on the electrophoretic images obtained as described in the previous sections. To verify the vector plasmid, pAAV-αMHCp-βGI-hrGFP-pA, was sequenced using the VIB service facility, which uses capillary sequencer (Applied Biosystems 3730 DNA Analyzer) in combination with ABI PRISM® BIG-DYE™ Terminator cycle sequencing kits for sequencing. Two forward and two reverse primers were used to sequence the αMHCp and the β-globin intron in the plasmid vector. The results obtained from the sequencing were aligned with a generated theoretical sequence, rAAV9 using CLUSTAL 2.0.11 multiple sequence alignment tools (complete alignment in Appendix 2). As shown below, primers 1 and 2 were designed to sequence the promoter whilst primers 4 and 5 were designed for the beta globin intron. The rAAV9 represents the sequence from the L-ITR to the R-ITR, thus, involving the promoter, the intron, the hrGFP and the BGHpA sequences. The sequences were confirmed to be correct.

Generation of pAAV-Reg-αMHCp-βGI-hrGFP-pA

The final construct for this research was the generation of expression cassette with the regulons (FIG. 6 [A]). The regulons were cloned in-between the L-ITR and the alpha myosin heavy chain promoter. As mentioned above, the vector was treated with phosphatase to prevent vector re-ligation since both ends of the vector fragment after the restriction with Acc65I would produce staggered ends which were very easy to ligate with each other. FIG. 6[B] is electrophoretic image showing the sizes of all the eight regulons, as well as the vector, pAAV-αMHCp-βGI-hrGFP-pA, before cloning. The bands obtained corresponded very well to the length of their theoretical sequences. In the order to which the wells have been numbered, numbers 1 to 8 corresponds to Myl3 (150 bp), Brd7 (689 bp), Myl2 (183 bp), Casq2e1 (219 bp), Casq2e2 (117 bp), Ankrd1e1 (299 bp), Ankrd1e2 (277 bp), and Ankrd1e3 (397), respectively.

Twenty resulting clones were screened after each cloning for positive clones, that is, the clone that contains the expected fragment size of the regulon and in the sense orientation, as well as the regulon not in tandem repeat. The electrophoretic image in FIG. 6[C] is the result of such screening after cloning to select the clones in the sense orientation. Since each of the regulon had MluI restriction site 12 bp to the end of it, and NdeI site located 20 bp to the end of the promoter, it was expected that every vector, which had the regulon cloned in the sense orientation, would produce a band of about 355 bp irrespective of the size of the regulon when the vector was digested with MluI-NdeI restriction enzymes. This observation is seen in the two bands shown in the red box of FIG. 6[C]. On the other hand, different bands were expected from clones of different vectors if the regulons were in the antisense orientation. In this case, the MluI site would be located 12 bp from the beginning of the regulon, which implies that, a restriction with MluI-NdeI endonucleases would cut almost the whole length of the particular regulon and the promoter. This would bring variations in the bands that would be generated from different vectors since each of the eight regulon has a different size. This particular image in FIG. 6[C] was the result after the Ankrd1e1 regulon was cloned into the vector pAAV-αMHCp-βGI-hrGFP-pA. With MluI-NdeI restriction on the pAAV-Ankrd1e1-αMHCp-βGI-hrGFP-pA vector clone, the clones with the regulons in the antisense orientation generated band of about 641 bp (FIG. 6[C], yellow box) which was expected since the Ankrd1e1 regulon has a size of 299 bp and the promoter with a size of 363 bp. The two bands in the blue box in this were as a result of an NdeI restriction site located inside the Ankrd1e1 regulon. It was the only regulon that contained an NdeI restriction site as revealed by MacVector software restriction analysis of the sequences of all the regulons. The second band, which is about 100 bp, resulted from fragments that were in-between the two NdeI sites in the vector, that is, one NdeI site in the promoter region and the second NdeI site in the regulon. The vectors with this regulon were further screened with other restriction enzymes, such as MluI-NheI.

After screening the vector clones based on sense orientation, the selected clones were tested using MluI endonuclease to check whether the regulons were in tandem. FIG. 6[D] shows one result obtained after positive clones were tested with MluI. It can be observed here that none of the selected positive clone had the regulon in tandem. If any was in tandem, a second band, which would be almost the size of the specific regulon in the vector, would be observed.

Electrophoretic image in FIG. 6 [E] shows duplicates of positive clones selected from five of the eight vectors to confirm the presence of the right regulon to be contained in respective vectors. With Acc65I restriction, each of the vectors was expected to produce a band that corresponds to the size of the particular regulon in the vector. The expected band sizes were (1) Brd7 of size 689 bp; (2) Casq2e1, 219 bp; (3) Ankrd1e1, 299 bp; (4) Ankrd1e2, 277 bp; and (5) Ankrd1e3, 397. This was observed in all the positive clones except clone 1 in the third well. This result reveals the significance of confirmatory tests. It must be noted that KpnI restriction also produced bands of the same sizes as by Acc65I because both Acc65I and KpnI restriction enzymes have the same recognition sequence, 5'-GGTACC-3' but whilst Acc65I cuts between the G-G, KpnI cuts between the C-C. The positive clones selected at the end of the confirmatory tests were thus proven to be of correct order, orientation and sizes and were therefore expanded for AAV vector production.

Example 2

Production and Titration of rAAV2/9 Vectors

Transfection Efficiencies of Vectors

Figure 7:
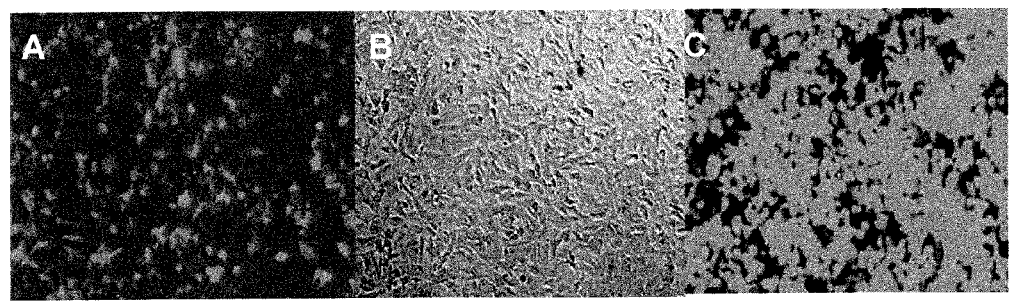
FIG. 7. Transfection efficiency in HEK 293 cells. [A] Expression of hrGFP at 24-hours post-transfection as viewed under the fluorescence microscope. [B] The transfected 293 cells under the microscope with normal white light showing about 99% confluence of cells. This background enabled the deduction of the transfection efficiency. [C] hrGFP expression after 48 hours transfection of HEK 293 cells showing about 95% transfection efficiency.

Each of the eight AAV plasmid vectors containing the regulons (pAAV-Reg-αMHCp-βGI-hrGFP-pA) and another control vector without any regulon (pAAV-αMHCp-βGI-hrGFP-pA) were extracted by MaxiPrep assay kit and later these purified plasmids were used for AAV vector production. An AAV vector encoding GFP under the control of cytomegalovirus (CMV) promoter was used as transfection and titration control in the AAV vector production. Each of the nine vectors was transfected together with adenovirus helper plasmid and AAV9 rep/cap plasmids by calcium phosphate precipitation into human embryonic kidney (HEK) 293 cells (known for its high transfection efficiency and protein production, and ability to carry out post-translational modifications, Thomas, et al., 2005). Transfection efficiency based on expression of the reporter gene, hrGFP of all vectors was determined 24- and 48-hour post-transfection. The potency of all vector constructs was ascertained at this level of transfection by the amount of cells transfected, termed transfection efficiency as observed under the fluorescence microscope. As shown in FIG. 7 and Table 3, all transfection yielded high transfection rate of about ninety percent (90%) or ninety-five percent (95%) after 48 hours of transfection making cells look almost all green (FIG. 7[C]). Such transfection efficiencies are considered very high, thus, signifies the success of transfection and confirms the potency of all the plasmid vector constructs.

Determination of Vector Titer by Q-PCR

Figure 8:
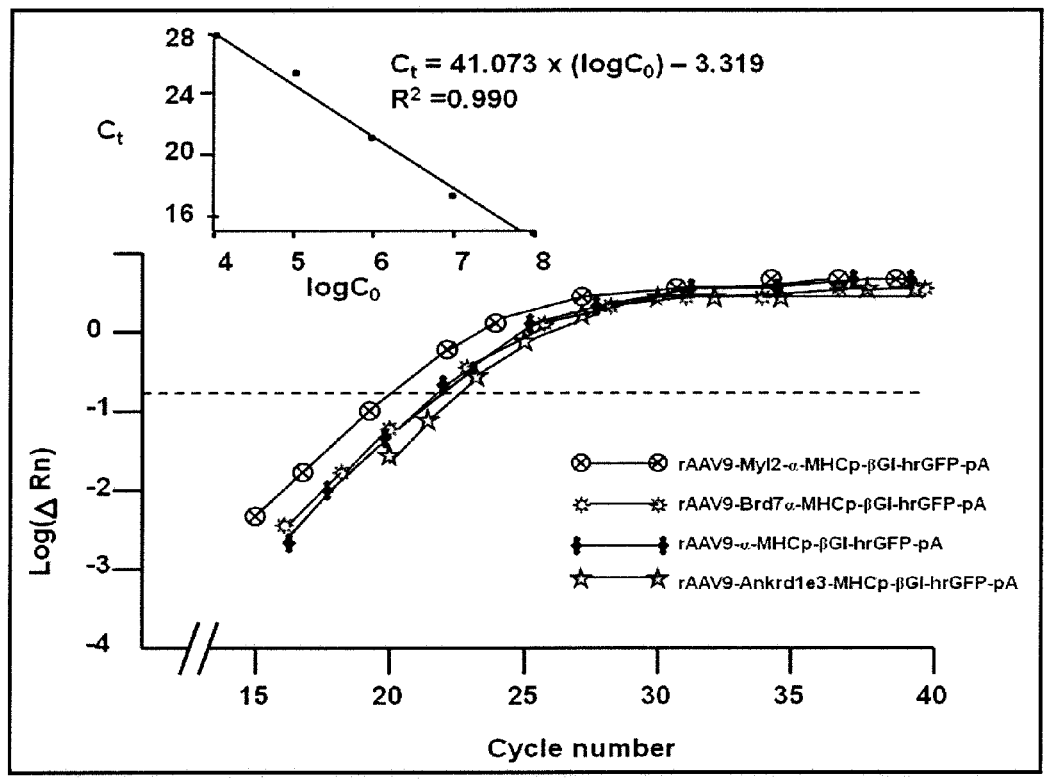
FIG. 8. Titration of 4 of the vectors with Q-PCR. The Q-PCR was performed in ABI7500 FAST (Sequencer Detector Unit from Applied Biosystems, Foster, Calif., USA) using ABI (PERKIM ELMER) Q-PCR master mix and TAQMAN probes and primers specific to detect bovine growth hormone polyA (BGH-polyA) as transgene DNA target sequence. Specific standards were prepared to get the standard curve and to calculate the signal on each of the sample, which in turn was used to determine the genomic copy number of respective vector.

AAV is known for its low titer from production and this make titration a very essential component of the AAV vectors production. With the standard graph (FIG. 8) and resulting $C_t$ values, the genomic copy number of each sample could be estimated. With a real-time PCR that utilizes a 20 well plate, copy numbers were expected to be ranging from $10^{11}$ to $10^{13}$ vg/ml. All values obtained (Table 3) were within the range and could therefore be used for in vivo experiments.

TABLE 3

Summary of transfection efficiencies and QPCR.

| Vector | Transfection efficiency (%) | Q-PCR (gc/ml) |
|---|---|---|
| pAAV-αMHCp-βGI-hrGFP-pA | 90 | $3.0 \times 10^{12}$ |
| pAAV-Myl3-αMHCp-βGI-hrGFP-pA | 95 | $2.7 \times 10^{11}$ |
| pAAV-Brd7-αMHCp-βGI-hrGFP-pA | 90 | $5.0 \times 10^{11}$ |
| pAAV-Myl2-αMHCp-βGI-hrGFP-pA | 90 | $3.5 \times 10^{11}$ |
| pAAV-Casq2e1-αMHCp-βGI-hrGFP-pA | 90 | $6.6 \times 10^{11}$ |
| pAAV-Casq2e2-αMHCp-βGI-hrGFP-pA | 95 | $6.6 \times 10^{12}$ |
| pAAV-Ankrd1e1-αMHCp-βGI-hrGFP-pA | 90 | $3.8 \times 10^{11}$ |
| pAAV-Ankrd1e2-αMHCp-βGI-hrGFP-pA | 90 | $1.17 \times 10^{11}$ |
| pAAV-Ankrd1e3-αMHCp-βGI-hrGFP-pA | 90 | $3.6 \times 10^{11}$ |

Transfection efficiencies of all the vectors and the amount of viral particles after cesium chloride gradient centrifugation are shown. The last column gives the genomic copy number (gc) of the vectors determined from real time PCR (qPCR). The regulons are indicated in RED.

Example 3

In Vivo Validation of rAAV9 Vectors

Figure 9:
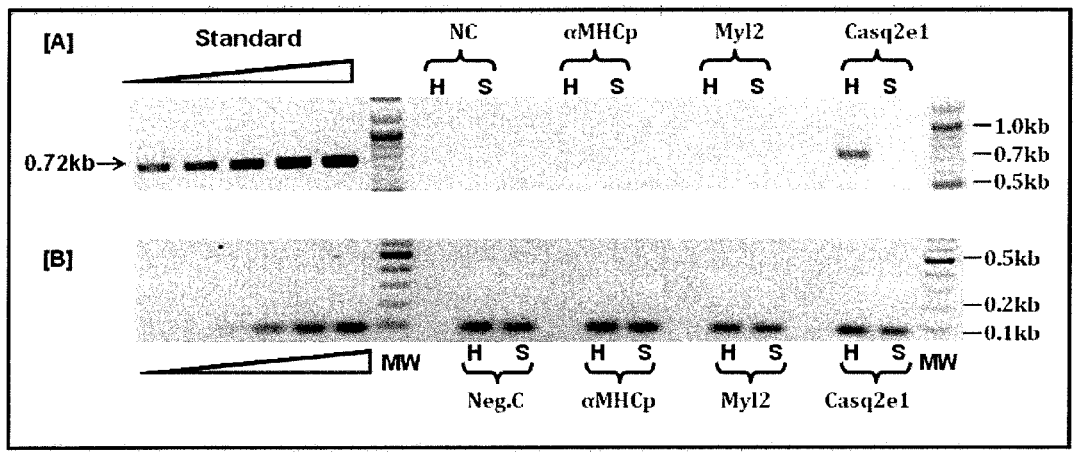
FIG. 9. Selective cardiac-specific expression by pAAV-Casq2e1-αMHCp-hrGFP-pA. GFP expression in the heart of all injected mice was confirmed by semi-quantitative RT-PCR. The heart of Casq2e1 vector showed prominent band corresponding to relatively robust expression of GFP transcripts in the heart. The heart of αMHCp and Myl2 injected mice showed fewer amounts of GFP transcripts. No GFP was observed in the spleen [A]. 0.8 kb GAPDH served as the internal control gene [B]. Serially diluted plasmid from which the hrGFP was amplified was used for the standard. Standard dye used for ladder was TryDye 2 Log from Westburg.

The AAV vectors containing the 8 different regulons and a control construct (with GFP driven by αMHC-promoter with no regulon: pAAV-αMHCp-βGI-hrGFP-pA were successfully produced with relatively good vector titer (Table 3). As a preliminary experiment, we tested only a low dose of $1.25 \times 10^{11}$ vg/mouse. Each of these vectors was injected intravenously via the tail vein into adult gamma C Nod-SCID null mice (Table 2). Reverse transcription polymerase chain reaction (RT-PCR) was used to detect the GFP expression of the different organs from the mice injected with the AAV vectors. Messenger RNAs (mRNA) were extracted from heart and spleen of the mice and hrGFP specific primers were used to reverse transcribe and amplify GFP cDNA. The resulting PCR products were visualized on agarose gel (FIG. 9). A prominent 716 bp band corresponding to GFP was detected from the heart tissue of the Casq2e1-regulon-containing vector whilst the heart tissues of the vector without regulon showed very minimal GFP cDNA in the heart tissues whilst none of the vectors showed any expression in the spleen (FIG. 9[A]). The Myl2-regulon-containing vector showed a modest increase in GFP mRNA compared to the control vector without regulon.

The test was normalized by the internal control gene, Glyceraldehyde 3-phosphate dehydrogenase (GAPDH). Quantification of the intensity of the bands after normalization with GAPDH, showed a very significant enhancement of the GFP expression by the novel Casq2e1 regulon. Casq2e1 regulon led to about 14 fold increased in GFP expression while the Myl2-regulon led to about 2 fold increased in GFP expression. Although the data shown here are only for the enhancers having SEQ ID NO:1 and 2, respectively, inclusion of regulons consistently led to augmentation of GFP expression from the αMHC promoter. This result further validates the successful prediction of regulons by the DDM data mining approach. This result also indicates that the regulons in combination with the αMHC promoter confer cardiac-specific expression.

Long-Term Follow-Up

To assess whether the enhancer elements not only increased cardiac-specific expression, but also ensured persistent (i.e., long-term) expression that remained tissue-specific, an initial experiment was set up in which GFP expression was evaluated 1 month post-injection (intravenous) of $2.5 \times 10^{10}$ AAV vector genomes in neonatal immuno-deficient NODSCID/gammaNull mice. The GFP fluorescence was assessed using an epifluorescence microscope, 1 month after vector injection (data not shown). SEQ ID NO:6 (the Ankrd1e3) was used as enhancer.

High level of cardiac GFP expression could be shown, whereas we detected no GFP expression in any of the other tissues. So both expression levels and specificity are maintained over a longer period.

Additional experiments using different doses (low: $10^{11}$, medium: $3 \times 10^{11}$ and high: $10^{12}$) were carried out to confirm the robustness and the specificity of each of the 8 enhancer elements (Table 3 above). AAV serotype 9 vectors for each of these enhancer elements were produced, titered and injected intravenously into 2-3 days old neonatal C57B16 mice. Mice were sacrificed 6 weeks post injection to determine the effect of each of the enhancer elements on the αMHC promoter. The control vector contains the GFP gene driven from the αMHC promoter without the enhancer element. All other vectors contain the GFP gene driven from the αMHC promoter where one enhancer element is cloned upstream of the αMHC promoter. After 6 weeks, with a weight between 17-21 grams, animals were euthanized by cervical dislocation and different organs were analyzed per mice (heart, muscle, liver, kidney, brain, spleen and diaphragm). Using the epifluorescence microscope, pictures at different values of exposure time were taken of complete heart. Some exemplary pictures are shown in FIG. 10, other data is available but not shown. All the organs were cut in several pieces and distributed in a 96-well plate to be analyzed under the confocal microscope. Microscopic analysis revealed that the expression was cardiac-specific, i.e., no or only very limited amounts of GFP were detected in organs other than heart for all enhancers (data not shown)

This provides compelling evidence indicating that the de novo identified cardiac enhancer elements (alias regulons) are cardiac specific and allow for high-level transgene expression in the heart.

Discussion

Eight different AAV constructs containing the regulons and one without regulon were successfully cloned and the corresponding AAV9 vectors were subsequently produced. All the clones were checked thoroughly and confirmed using multiple restriction enzymes analysis. Positive clones were further confirmed by DNA sequencing. During production of the AAV vectors, 90% transfection efficiency was achieved 48 hours after transfection indicating that the plasmid DNA extraction was well performed leading to high purity DNA for transfection. This step is crucial to achieve high AAV vector titers after production. Titration analyses of all the AAV9 vectors indicated high vector titer (Table 3 and data not shown) (range: $3 \times 10^{11}$ to $10^{13}$ vg/ml) consistent with previously reported studies (VandenDriessche et al., 2007). These vector doses were sufficient to initiate a preliminary in vivo experiment in the murine model. Since in vitro results cannot always be extrapolated to in vivo observations, we chose not to conduct any in vitro pre-validation studies in cardiac cell lines but instead focused on direct AAV9 gene delivery in vivo.

In a first preliminary experiment, immunodeficient mice (that is, NOD-SCID γc$^{-/-}$) were used. The rationale for using NOD-SCID γc$^{-/-}$ mice is justified to avoid any immune response towards the transduced cardiomyocytes.

In this study, a low dose of $1.25 \times 10^{11}$ vg AAV9/mouse was systemically administered to the mice. Using confocal microscopic analysis, in vivo GFP expression was detected in the heart but not in other organs, such as liver, brain and muscle.

In this first experiment, three different AAV constructs encoding GFP driven from the heart specific promoters were tested. Two constructs containing regulons designated as rAAV9-Casqe1-αMHC and rAAV9-Myl2-αMHC were tested and one control construct with no regulon and just the basic αMHC promoter was used for comparison (rAAV9-αMHC). The RT-PCR data indicate that the inclusion of Casq2e1 and Myl2-regulon upstream of the α-MHC promoter augmented the expression of the promoter (FIG. 9), with Casq2e1 being the most robust regulon. Our data also suggest that the novel data-mining algorithm based on a distance difference matrix (DDM) could lead to the identification of novel heart-specific TFBS associations and selection of heart specific regulons. These "regulons" contain a high percentage of heart-specific TFBS associations, as a common denominator among highly expressed heart-specific genes. Moreover, these regulons are evolutionary conserved among divergent species, suggesting strong Darwinian selective pressure to maintain these particular TFBS combinations for high heart expression. The heart-specificity of the regulon was also confirmed by RT-PCR indicating selective GFP mRNA expression in the heart but not in any other tissue (FIG. 9). This effect is maintained in longer-term follow-up (data not shown).

Figure 10A:
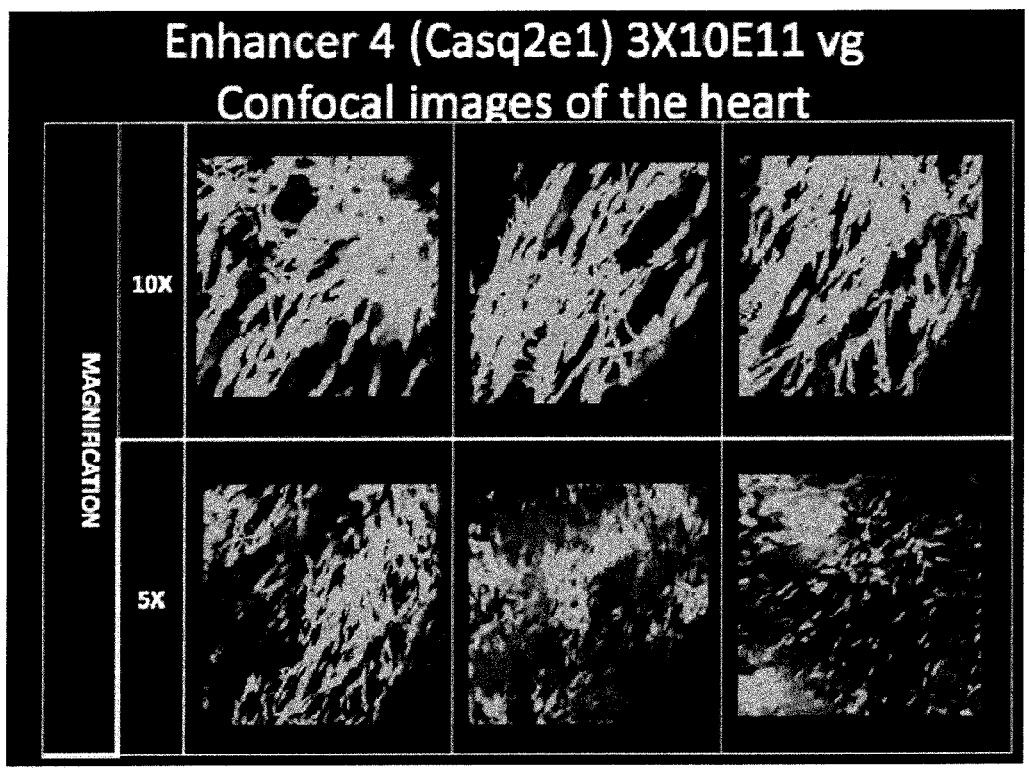
FIG. 10. Comparative analysis of long-term cardiac-specific GFP expression. Confocal microscopy data showing hearts of mice injected with medium dose of AAV-Casq2e1-αMHCp-βGI-hrGFP-pA (i.e., using enhancer 4, SEQ ID NO:1) (A), AAV-Ankrd1e2-αMHCp-βGI-hrGFP-pA (i.e., using enhancer 7, SEQ ID NO:5) (B) and with high dose of reference vector AAV-αMHCp-βGI-hrGFP-pA (C).
Figure 10B:
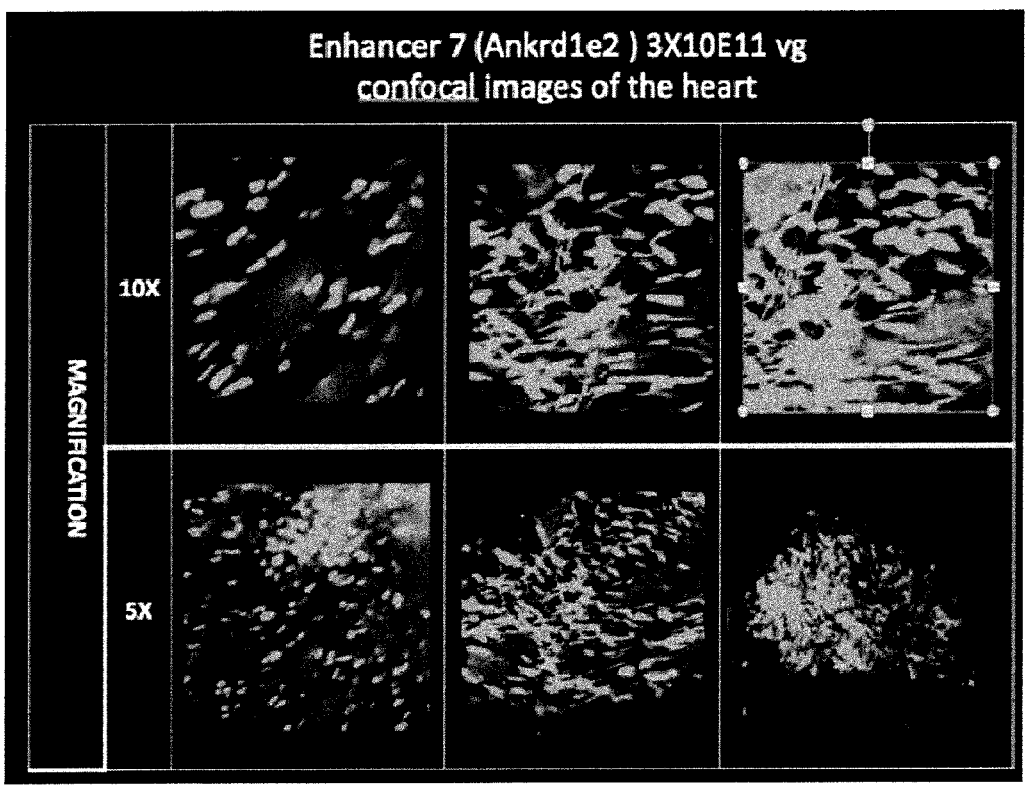
Figure 10C:
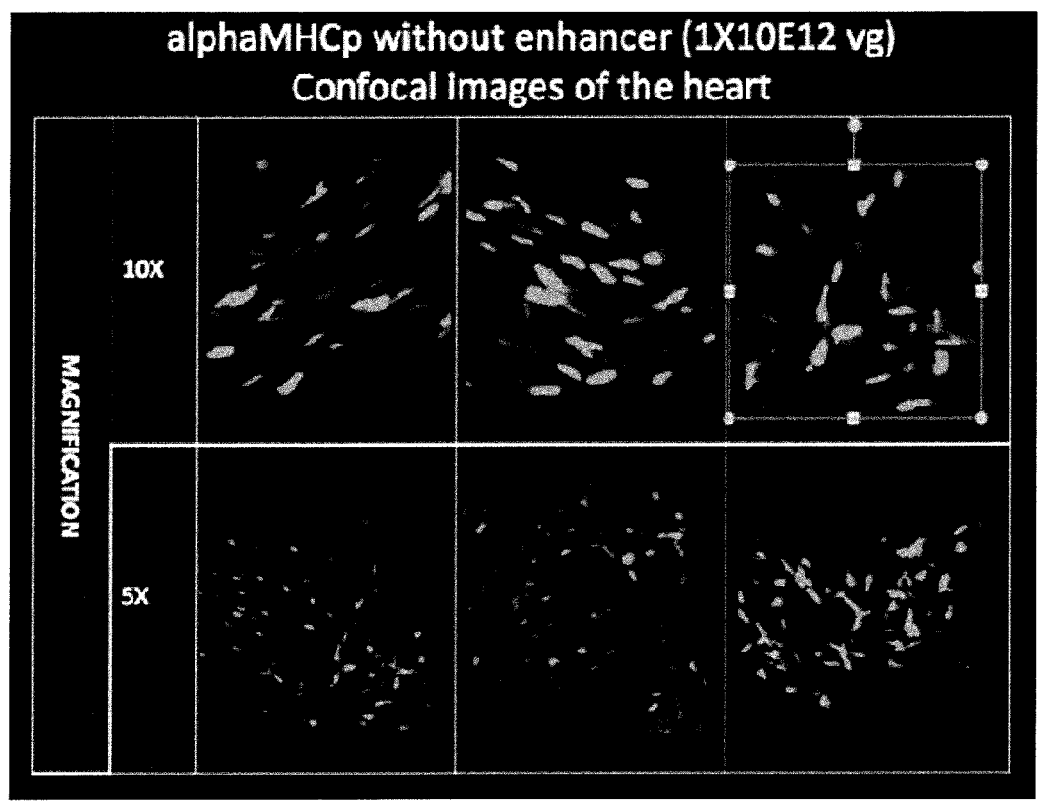
Figure 11:
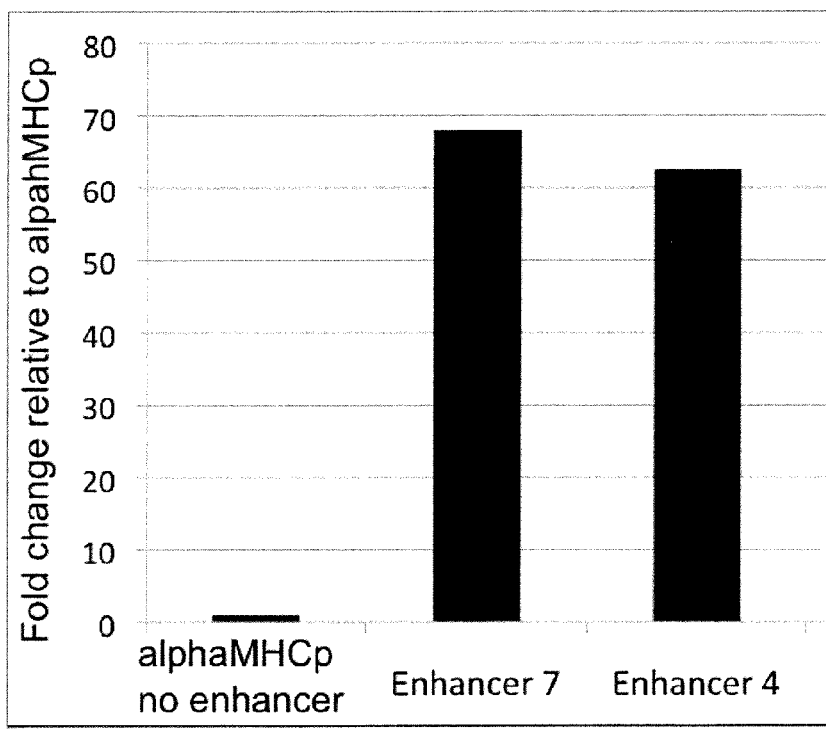
FIG. 11. Comparative analysis of long-term cardiac-specific GFP expression by quantitative RT-PCR. AAV-Casq2e1-αMHCp-βGI-hrGFP-pA and AAV-Ankrd1e2-αMHCp-βGI-hrGFP-pA are compared with reference vector AAV-αMHCp-βGI-hrGFP-pA, as in FIG. 10.

In follow-on experiments, both lower ($2 \times 10^{10}$ vg AAV9/mouse) and higher ($3 \times 10^{11}$ vg AAV9/mouse) doses of the viral constructs were used. Also, C57B16 mice were used instead of NOD-SCID mice. All eight enhancers showed robust increase of expression in vivo as compared to control (FIGS. 10 and 11 and data not shown). The control (containing the αMHC promoter without enhancer) was used at 3 different concentrations ($2 \times 10^{10}$ vg AAV9/mouse, $3 \times 10^{11}$ vg AAV9/mouse and $1 \times 10^{12}$ vg AAV9/mouse) and the vectors with enhancer resulted in higher expression of the GFP transgene, even when comparing to considerable higher amounts of control vector (FIGS. 10A-C). The GFP data are representative of at least two mice. Although all eight enhancers considerably increased promoter expression, two enhancers reproducibly performed better than the others. In all these experiments using different doses, enhancer Casq2e1 consistently led to the most robust GFP expression (FIG. 10A) in all the mice tested. The second most robust GFP expression comes from the Ankrd1e2 enhancer and is consistently the second best out of the 8 enhancers tested (FIG. 10B). The GFP expression driven by these two enhancer-promoter combinations was quantified by RT-PCR and compared to control. Results are shown in FIG. 11. Although these data are only from one mouse (explaining why the Ankrd1e2 enhancer (enhancer 7) appears to perform slightly better than the Casq2e1 enhancer (enhancer 4), in contrast to the fluorescence data), both enhancer-containing expression cassettes express over 60 times more GFP than the same vector without enhancer.

These data demonstrate the increased efficiency of the vectors with enhancers, and proves that the use of these enhancer sequences is not only more economical, but is also more likely to have a better safety profile, since lower vector doses are needed to achieve efficient gene transfer in vivo in the heart. Moreover, for all enhancers, this increase in expression is cardiac-specific, as no significant expression was found in other organs—i.e., no "leakage" was observed. This was determined by looking at expression in liver, lung, kidney, muscle, spleen and diaphragm (data not shown).

This study demonstrates that an integrative approach combining differential screening, rational in silico promoter analysis and design followed by semi high-throughput in vivo screening can result in robust tissue-specific gene delivery vectors, which may be generally applicable to different target tissues and vectors.

Since the GFP transgene product is a foreign, xenogeneic antigen, its expression in transduced cardiomyocytes could potentially elicit cytotoxic T cell responses specific for the GFP antigenic peptides presented in association with major histocompatibility complex (MHC) class I antigens. These immune responses may ultimately result in the elimination of the transduced cardiomyocytes and skew the interpretation of the related data comparing different regulons. This is why NOD-SCID $\gamma c^{-/-}$ mice were initially used here. It is therefore unlikely that cellular immune responses influenced the extent and persistence of GFP-transduced cardiomyocytes in the present study. For the same reason, it can also be excluded that anti-AAV antibodies would have interfered with AAV transduction. These results could be recapitulated in non-immunodeficient mice.

In conclusion, the present study suggests that the novel regulons in combination with αMHC promoter delivered by AAV9 vectors are able to force transgene expression to the heart. Hence, the restricted expression in the heart is not attributable only to the use of AAV9 (tropic for the heart) but also requires the use of the αMHC (cardiac-specific) in conjunction with a cardiac specific regulon allowing restriction of transgene expression to the myocardium.

Importantly, although part of the present results have been obtained with immunodeficient mice, this was only in view of the xenogeneic nature of the expressed protein. When a non-foreign agent is transduced (e.g., a therapeutic protein), it is not necessarily required to suppress the immune response to practice the methods, described herein, as shown by the experiments in C57B16 mice (although concomitant immune suppression is envisaged as well, e.g., to avoid interfering with transduction efficiency due to a reaction against the (viral) vector).

REFERENCES

Aikawa, R., Huggins, G. S., & Snyder, R. O. (2002). Cardiomyocyte-specific gene expression following recombinant adeno-associated viral vector transduction. J Biol Chem, 277(21), 18979-18985.
Antoniou, M., Geraghty, F., Hurst, J., & Grosveld, F. (1998). Efficient 3'-end formation of human beta-globin mRNA in vivo requires sequences within the last intron but occurs independently of the splicing reaction. Nucleic Acids Res, 26(3), 721-729.
Ausubel et al., Current Protocols in Molecular Biology (Supplement 47), John Wiley & Sons, New York (1999).
Berger S L, Kimmel A R. Guide to Molecular Cloning Techniques. Methods in Enzymology, vol. 152, Academic Press, Inc., San Diego, Calif., 1987.
Black, R. G., Jr., Guo, Y., Ge, Z. D., Murphree, S. S., Prabhu, S. D., Jones, W. K., Bolli, R., & Auchampach, J. A. (2002). Gene dosage-dependent effects of cardiac-specific overexpression of the A3 adenosine receptor. Circ Res, 91(2), 165-172.
Bostick, B., Yue, Y., Long, C., Marschalk, N., Fine, D. M., Chen, J., & Duan, D. (2009). Cardiac expression of a mini-dystrophin that normalizes skeletal muscle force only partially restores heart function in aged Mdx mice. Mol Ther, 17(2), 253-261.
Buerger, A., Rozhitskaya, O., Sherwood, M. C., Dorfman, A. L., Bisping, E., Abel, E. D., Pu, W. T., Izumo, S., & Jay, P. Y. (2006). Dilated cardiomyopathy resulting from high-level myocardial expression of Cre-recombinase. J Card Fail, 12(5), 392-398.
Buzina, A., Lo, M. Y., Moffett, A., Hotta, A., Fussner, E., Bharadwaj, R. R., Pasceri, P., Garcia-Martinez, J. V., Bazett-Jones, D. P., & Ellis, J. (2008). Beta-globin LCR and intron elements cooperate and direct spatial reorganization for gene therapy. PLoS Genet, 4(4), e1000051.
Cao, L., During, M., & Xiao, W. (2002). Replication competent helper functions for recombinant AAV vector generation. Gene Ther, 9(18), 1199-1206.
Cristiano R J, Smith L C, Kay M A, Brinkley B R, Woo S L. Hepatic gene therapy: efficient gene delivery and expression in primary hepatocytes utilizing a conjugated adenovirus-DNA complex. Proc Natl Acad Sci USA. 1993 Dec. 15; 90(24):11548-52.
De Bleser P, Hooghe B, Vlieghe D, van Roy F. A distance difference matrix approach to identifying transcription factors that regulate differential gene expression. Genome Biol. 2007; 8(5):R83.
Dishart, K. L., Work, L. M., Denby, L., & Baker, A. H. (2003). Gene Therapy for Cardiovascular Disease. J Biomed Biotechnol, 2003(2), 138-148.
Douar, A. M., Poulard, K., Stockholm, D., & Danos, O. (2001). Intracellular trafficking of adeno-associated virus vectors: routing to the late endosomal compartment and proteasome degradation. J Virol, 75(4), 1824-1833.
Fomicheva, E. V., Turner, I I, Edwards, T. G., Hoff, J., Arden, E., D'Alecy, L. G., & Metzger, J. M. (2008). Double oxygen-sensing vector system for robust hypoxia/ischemia-regulated gene induction in cardiac muscle in vitro and in vivo. Mol Ther, 16(9), 1594-1601.
Goehringer, C., Rutschow, D., Bauer, R., Schinkel, S., Weichenhan, D., Bekeredjian, R., Straub, V., Kleinschmidt, J. A., Katus, H. A., & Muller, O. J. (2009). Prevention of cardiomyopathy in delta-sarcoglycan knockout mice after systemic transfer of targeted adeno-associated viral vectors. Cardiovasc Res, 82(3), 404-410.
Gruber, P. J., Li, Z., Li, H., Worrad, D., Huang, B., Abdullah, I., Wang, W., El-Deiry, W., Ferrari, V. A., & Zhou, R. (2004). In vivo imaging of MLC2v-luciferase, a cardiac-specific reporter gene expression in mice. Acad Radiol, 11(9), 1022-1028.
Gruh, I., Wunderlich, S., Winkler, M., Schwanke, K., Heinke, J., Blomer, U., Ruhparwar, A., Rohde, B., Li, R. K., Haverich, A., & Martin, U. (2008). Human CMV immediate-early enhancer: a useful tool to enhance cell-type-specific expression from lentiviral vectors. J Gene Med, 10(1), 21-32.
Inagaki, K., Fuess, S., Storm, T. A., Gibson, G. A., McTiernan, C. F., Kay, M. A., & Nakai, H. (2006). Robust systemic transduction with AAV9 vectors in mice: efficient global cardiac gene transfer superior to that of AAV8. Mol Ther, 14(1), 45-53.
Jacques, A. M., Briceno, N., Messer, A. E., Gallon, C. E., Jalilzadeh, S., Garcia, E., Kikonda-Kanda, G., Goddard, J., Harding, S. E., Watkins, H., Esteban, M. T., Tsang, V. T., McKenna, W. J., & Marston, S. B. (2008). The molecular phenotype of human cardiac myosin associated with hypertrophic obstructive cardiomyopathy. Cardiovasc Res, 79(3), 481-491.
Jenke A C, Stehle I M, Herrmann F, Eisenberger T, Baiker A, Bode J, Fackelmayer F O, Lipps H J. Nuclear scaffold/matrix attached region modules linked to a transcription unit are sufficient for replication and maintenance of a mammalian episome. Proc Natl Acad Sci USA. 2004 Aug. 3; 101(31):11322-7.

Kel A E, Gössling E, Reuter I, Cheremushkin E, Kel-Margoulis O V, Wingender E. MATCH: A tool for searching transcription factor binding sites in DNA sequences. Nucleic Acids Res. 2003 Jul. 1; 31(13):3576-9.

Krum H. and Abraham W. T., (2009). Heart failure. Lancet, 373(9667), 941-955.

Kwon, I., & Schaffer, D. V. (2008). Designer gene delivery vectors: molecular engineering and evolution of adeno-associated viral vectors for enhanced gene transfer. Pharm Res, 25(3), 489-499.

LaPointe, M. C., Yang, X. P., Carretero, O. A., & He, Q. (2002). Left ventricular targeting of reporter gene expression in vivo by human BNP promoter in an adenoviral vector. Am J Physiol Heart Circ Physiol, 283(4), H1439-1445.

Lyon, A. R., Sato, M., Hajjar, R. J., Samulski, R. J., & Harding, S. E. (2008). Gene therapy: targeting the myocardium. Heart, 94(1), 89-99.

Manzini S, Vargiolu A, Stehle I M, Bacci M L, Cerrito M G, Giovannoni R, Zannoni A, Bianco M R, Forni M, Donini P, Papa M, Lipps H J, Lavitrano M. Genetically modified pigs produced with a nonviral episomal vector. Proc Natl Acad Sci USA. 2006 Nov. 21; 103(47):17672-7.

Miller A D. Retrovirus packaging cells. Hum Gene Ther. 1990 Spring; 1(1):5-14.

Naldini L, Blömer U, Gallay P, Ory D, Mulligan R, Gage F H, Verma I M, Trono D. In vivo gene delivery and stable transduction of non-dividing cells by a lentiviral vector. Science. 1996 Apr. 12; 272(5259):263-7.

Pacak, C. A., Sakai, Y., Thattaliyath, B. D., Mah, C. S., & Byrne, B. J. (2008). Tissue specific promoters improve specificity of AAV9 mediated transgene expression following intra-vascular gene delivery in neonatal mice. Genet Vaccines Ther, 6, 13.

Pacak, C. A., Sakai, Y., Thattaliyath, B. D., Mah, C. S., & Byrne, B. J. (2009). Tissue specific promoters improve specificity of AAV9 mediated transgene expression following intra-vascular gene delivery in neonatal mice. Genet Vaccines Ther, 7, 3. (correction on Pacak et al., 2008)

Papatsenko D A, Makeev V J, Lifanov A P, Régnier M, Nazina A G, Desplan C. Extraction of functional binding sites from unique regulatory regions: the *Drosophila* early developmental enhancers. Genome Res. 2002 March; 12(3):470-81.

Phillips, M. I., Tang, Y., Schmidt-Ott, K., Qian, K., & Kagiyama, S. (2002). Vigilant vector: heart-specific promoter in an adeno-associated virus vector for cardioprotection. Hypertension, 39(2 Pt 2), 651-655.

Pilpel Y, Sudarsanam P, Church G M. Identifying regulatory networks by combinatorial analysis of promoter elements. Nat Genet. 2001 October; 29(2):153-9.

Raake, P. W., Hinkel, R., Muller, S., Delker, S., Kreuzpointner, R., Kupatt, C., Katus, H. A., Kleinschmidt, J. A., Boekstegers, P., & Muller, O. J. (2008). Cardio-specific long-term gene expression in a porcine model after selective pressure-regulated retroinfusion of adeno-associated viral (AAV) vectors. Gene Ther, 15(1), 12-17.

Reynolds, P. N., Nicklin, S. A., Kaliberova, L., Boatman, B. G., Grizzle, W. E., Balyasnikova, I. V., Baker, A. H., Danilov, S. M., & Curiel, D. T. (2001). Combined transductional and transcriptional targeting improves the specificity of transgene expression in vivo. Nat Biotechnol, 19(9), 838-842.

Salva, M. Z., Himeda, C. L., Tai, P. W., Nishiuchi, E., Gregorevic, P., Allen, J. M., Finn, E. E., Nguyen, Q. G., Blankinship, M. J., Meuse, L., Chamberlain, J. S., & Hauschka, S. D. (2007). Design of tissue-specific regulatory cassettes for high-level rAAV-mediated expression in skeletal and cardiac muscle. Mol Ther, 15(2), 320-329.

Sambrook et al., Molecular Cloning: A Laboratory Manual, $2^{nd}$ ed., Cold Spring Harbor Press, Plainsview, N.Y. (1989).

Sasano, T., Kikuchi, K., McDonald, A. D., Lai, S., & Donahue, J. K. (2007). Targeted high-efficiency, homogeneous myocardial gene transfer. J Mol Cell Cardiol, 42(5), 954-961.

Stewart, D. J., Kutryk, M. J., Fitchett, D., Freeman, M., Camack, N., Su, Y., Della Siega, A., Bilodeau, L., Burton, J. R., Proulx, G., & Radhakrishnan, S. (2009). VEGF gene therapy fails to improve perfusion of ischemic myocardium in patients with advanced coronary disease: results of the NORTHERN trial. Mol Ther, 17(6), 1109-1115.

Su, H., Joho, S., Huang, Y., Barcena, A., Arakawa-Hoyt, J., Grossman, W., & Kan, Y. W. (2004). Adeno-associated viral vector delivers cardiac-specific and hypoxia-inducible VEGF expression in ischemic mouse hearts. Proc Natl Acad Sci USA, 101(46), 16280-16285.

Thomas, P., & Smart, T. G. (2005). HEK293 cell line: a vehicle for the expression of recombinant proteins. J Pharmacol Toxicol Methods, 51(3), 187-200.

Trapnell B C. Adenoviral vectors for gene transfer. Adv. Drug Del. Rev. 1993 12: 185-199.

VandenDriessche T, Thorrez L, Acosta-Sanchez A, Petrus I, Wang L, Ma L, De Waele L, Iwasaki Y, Gillijns V, Wilson J M, Collen D, Chuah M K. Efficacy and safety of adeno-associated viral vectors based on serotype 8 and 9 vs. lentiviral vectors for hemophilia B gene therapy. J Thromb Haemost. 2007 January; 5(1):16-24.

Vassalli, G., Roehrich, M. E., Vogt, P., Pedrazzini, G. B., Siclari, F., Moccetti, T., & von Segesser, L. K. (2009). Modalities and future prospects of gene therapy in heart transplantation. Eur J Cardiothorac Surg, 35(6), 1036-1044.

Venter, M. (2007). Synthetic promoters: genetic control through cis engineering. Trends Plant Sci, 12(3), 118-124.

Wang, B., Li, J., Fu, F. H., Chen, C., Zhu, X., Zhou, L., Jiang, X., & Xiao, X. (2008). Construction and analysis of compact muscle-specific promoters for AAV vectors. Gene Ther, 15(22), 1489-1499.

Wang, Y., Ebermann, L., Sterner-Kock, A., Wika, S., Schultheiss, H. P., Dorner, A., & Walther, T. (2009). Myocardial overexpression of adenine nucleotide translocase 1 ameliorates diabetic cardiomyopathy in mice. Exp Physiol, 94(2), 220-227.

Xu, Z. L., Mizuguchi, H., Ishii-Watabe, A., Uchida, E., Mayumi, T., & Hayakawa, T. (2001). Optimization of transcriptional regulatory elements for constructing plasmid vectors. Gene, 272(1-2), 149-156.

Yamada T, Iwasaki Y, Tada H, Iwabuki H, Chuah M K, VandenDriessche T, Fukuda H, Kondo A, Ueda M, Seno M, Tanizawa K, Kuroda S. Nanoparticles for the delivery of genes and drugs to human hepatocytes. Nat Biotechnol. 2003 August; 21(8):885-90.

Yue, Y., Ghosh, A., Long, C., Bostick, B., Smith, B. F., Kornegay, J. N., & Duan, D. (2008). A single intravenous injection of adeno-associated virus serotype-9 leads to whole body skeletal muscle transduction in dogs. Mol Ther, 16(12), 1944-1952.

The invention claimed is:

1. A nucleic acid expression cassette comprising at least one nucleic acid regulatory element of 300 nucleotides or less for enhancing cardiac-specific gene expression, wherein the nucleic acid regulatory element is selected from the group consisting of: SEQ ID NO: 1, SEQ ID NO: 3, SEQ ID NO: 4, SEQ ID NO: 5, SEQ ID NO: 8 and a sequence having 95% identity to any one of SEQ ID NO: 1, SEQ ID NO: 3, SEQ ID NO: 4, SEQ ID NO: 5 and SEQ ID NO: 8, and wherein the nucleic acid regulatory element is operably linked to a promoter and a transgene.

2. The nucleic acid expression cassette of claim 1, wherein the nucleic acid regulatory element is SEQ ID NO: 1 or a sequence having 95% identity thereto.

3. The nucleic acid expression cassette of claim 1, wherein the nucleic acid regulatory element is 250 nucleotides or less.

4. A nucleic acid expression cassette comprising two or more nucleic acid regulatory elements each of 300 nucleotides or less for enhancing cardiac-specific gene expression, wherein the nucleic acid regulatory elements are selected from the group consisting of: SEQ ID NO: 1, SEQ ID NO: 3, SEQ ID NO: 4, SEQ ID NO: 5, SEQ ID NO: 8 and a sequence having 95% identity to any one of SEQ ID NO: 1, SEQ ID NO: 3, SEQ ID NO: 4, SEQ ID NO: 5 and SEQ ID NO: 8, and wherein each of the nucleic acid regulatory element is operably linked to a promoter and a transgene.

5. The nucleic acid expression cassette of claim 4, wherein the two or more nucleic acid regulatory elements are identical.

6. The nucleic acid expression cassette of claim 1, wherein the promoter is a cardiac-specific promoter.

7. The nucleic acid expression cassette of claim 6, wherein the promoter is from the myosin heavy chain gene.

8. The nucleic acid expression cassette of claim 1, additionally comprising a β-globin intron.

9. The nucleic acid expression cassette of claim 1, wherein the transgene encodes a therapeutic protein.

10. A vector comprising the nucleic acid expression cassette of claim 1.

11. A vector comprising: a nucleic acid regulatory element of 300 nucleotides or less selected from the group consisting of: SEQ ID NO: 1, SEQ ID NO: 3, SEQ ID NO: 4, SEQ ID NO: 5, SEQ ID NO: 8 and a sequence having 95% identity to any one of SEQ ID NO: 1, SEQ ID NO: 3, SEQ ID NO: 4, SEQ ID NO: 5 and SEQ ID NO: 8, and wherein the nucleic acid regulatory element is operably linked to a promoter and a transgene.

12. The vector according to claim 11, which is a viral vector.

13. The vector according to claim 12, which is an AAV9 vector or an AAV2/9 vector.

14. A method for expressing a protein in a heart cell, the method comprising: introducing into at least one heart cell the nucleic acid expression cassette of claim 1; and expressing the transgene protein product thereof in the heart cell.

15. The method according to claim 14, wherein the protein is expressed in vivo.

16. The nucleic acid expression cassette of claim 7, wherein the promoter is from the myosin heavy chain alpha (αMHC) gene.

17. The nucleic acid expression cassette of claim 9, wherein the therapeutic protein is selected from the group consisting of an angiogenic factor, VEGF, PlGF, an ATPase, SERCA2a, an ion channel, a cytokine, and a growth factor.

18. The vector of claim 12, wherein the vector is a lentiviral or an AAV vector.

19. A vector comprising: a nucleic acid expression cassette comprising at least one nucleic acid regulatory element of 300 nucleotides or less, wherein the nucleic acid regulatory element is selected from the group consisting of: SEQ ID NO: 1, SEQ ID NO: 3, SEQ ID NO: 4, SEQ ID NO: 5, SEQ ID NO: 8 and sequence having 95% identity to any one of SEQ ID NO: 1, SEQ ID NO: 3, SEQ ID NO: 4, SEQ ID NO: 5 and SEQ ID NO: 8, and wherein the nucleic acid regulatory element is operably linked to a promoter and a transgene.

20. An isolated nucleic acid regulatory element of 300 nucleotides or less for enhancing cardiac-specific gene expression, wherein the nucleic acid regulatory element is selected from a sequence having between 95% and 99% identity to any one of SEQ ID NO: 1, SEQ ID NO: 3, SEQ ID NO: 4, SEQ ID NO: 5 and SEQ ID NO: 8, and wherein the nucleic acid regulatory element is operably linked to a promoter and a transgene.

21. A pharmaceutical composition comprising the nucleic acid expression cassette of claim 9, and a pharmaceutically acceptable carrier.

* * * * *

SEQUENCE LISTING

<160> NUMBER OF SEQ ID NOS: 30

<210> SEQ ID NO 1
<211> LENGTH: 192
<212> TYPE: DNA
<213> ORGANISM: Homo sapiens

<400> SEQUENCE: 1
agtagaaaaa cagccaagct agggaggctg ggaggccaag ccccagatac cttacatagc    60
tctgctcagc ctctgtctca ttaggaactc cattttttagg atgcagttgt ttcaggctaa   120
aaataaatca tgcaatgaat aaaaaagtta gatacgacac tgtagaggga ttcgctgata   180
cagtctgtcc ga                                                        192

<210> SEQ ID NO 2
<211> LENGTH: 156
<212> TYPE: DNA
<213> ORGANISM: Homo sapiens

<400> SEQUENCE: 2
ccagctctct gcagcccagg aacaataaat acttcctccc catgtttaaa aataacccca    60
tgaccgcttt tggcagtcat aggtgaggcg ggcaccacct aaggcccccc caccccatgc   120
cgttcttctg aagtaagggt ggctcactcg ccactg                              156

<210> SEQ ID NO 3
<211> LENGTH: 90
<212> TYPE: DNA
<213> ORGANISM: Homo sapiens

<400> SEQUENCE: 3
attattcttt ttttacaaag cgttttcttt ccttattatt tattttttgct tgggctaatt   60 ttaaaatgag tttttattcc cttggtacaa                                     90

<210> SEQ ID NO 4
<211> LENGTH: 272
<212> TYPE: DNA
<213> ORGANISM: Homo sapiens

<400> SEQUENCE: 4
tgaatcagga agaaatgtga gagggccatt cctttggtgg tgatcacatc gctcagcaat    60
gcaagtcatc ctatttgtca agagtcaggg gacagctgtc tgttgacatt gcaccacatc   120
actgcccttt ttttctttgt cagctttcat atgactacct atcaagaaaa tgtagatgcc   180
ctacatatca cacccccagt aatatctttc tgataagcag acttatcaac acttcactta   240
ggggaaactt gtcccaggac atcctattcc ct                                  272

<210> SEQ ID NO 5
<211> LENGTH: 250
<212> TYPE: DNA
<213> ORGANISM: Homo sapiens

<400> SEQUENCE: 5
gattgtcata gtaacgctct gaaaagattt tgatgcaact ttggaattac ttcacaccca    60
attacataga acatctactt ggaatgagag ataagtgctt ctgtgactgc aaacatagat   120
agaaaatcca ttaaccttttt tagccattta ttaaagcaga ggaaaattat ttttaaaatg   180
caatttctga cttcaagaag aagtaccgaa aaaatatttt tcttggtgta gtttggagtt   240
tcctaataaa                                                           250

<210> SEQ ID NO 6
<211> LENGTH: 370
<212> TYPE: DNA
<213> ORGANISM: Homo sapiens

<400> SEQUENCE: 6

```
aagatgatgt ccttccttat ttggtggctc tggaagccac attccctcct catccgcctt      60
cccaaaagaa ccttgtggct gcccagcgga agccagtgct ttcagcagcc cccacccttg     120
gcatttcctt atctaggagt cttcactgtg gaattccaag gcccacccca atgctccgga     180
tgtgtttcaa tccatggcct gccactttgt tactcttgtg atgacaagca gataacatag     240
ctcacatgcc ttcttttcct gcataccaac cagaccccag ttctgaaaag gaaacaaacc     300
acaaaccaag agagatgtgt tattttttatg cagacattgt taagacactg caataagcct     360
agaattgtgg                                                            370
```

<210> SEQ ID NO 7
<211> LENGTH: 662
<212> TYPE: DNA
<213> ORGANISM: Homo sapiens

<400> SEQUENCE: 7

```
tccagtcagg cccgcctgag attacctagg tgttctggtg acttctgagg gcctcgcatg      60
aaagataacg cccaaatcaa caaatctgcc attgtggctt tgaagagact gtttcaatca     120
ctttattttg tctttatgtc aggttttgcca gatggcttgg gtctttctga ggtcctgtac     180
cgagggggca cagagagaac tggtgcagct tcaaagctcc tttttaatct ttagcaacat     240
cacagcggct gggaaactgc ctcggctccc tcaagtctct cccacaaaag aggcgcggcc     300
gaggctctaa tgaaagccag ataaagggat ggctggaatc agaaacagag ggaaaagagc     360
agtcgttagt cttcttgta gctgtttcaa aagaaattct aagacaaatt atggctttgg     420
gtgttttct aaaaggactg cagcagggag aggaggtggg ggaggtgctt tgaccccctca     480
gcacccttcc ccttgcatga aaggcagagg agactgaaaa aaggctgaaa tacaacaata     540
aactttctgc ttgtgcgcgt ggggatgaaa ggcgcgctgg cataattatg ggcgagggtg     600
cgcgggggcg ggcgggcggc tttaccttgc cgccagcgct attaatgatg aggctccctc     660
tt                                                                    662
```

<210> SEQ ID NO 8
<211> LENGTH: 123
<212> TYPE: DNA
<213> ORGANISM: Homo sapiens

<400> SEQUENCE: 8

```
acctcatgac cccagcccca cccctgcagt gcacaatagg gacagggcca taaaggata       60
tggctaggct tagggctat tttggggcct ggggagggca ttgttcaggc tcaggaatgg     120
gta                                                                   123
```

<210> SEQ ID NO 9
<211> LENGTH: 218
<212> TYPE: DNA
<213> ORGANISM: Artificial Sequence
<220> FEATURE:
<223> OTHER INFORMATION: Regulon and restriction site

```
<400> SEQUENCE: 9
ggtaccggcg cgccagtaga aaaacagcca agctagggag gctgggaggc caagccccag    60
ataccttaca tagctctgct cagcctctgt ctcattagga actccatttt taggatgcag   120
ttgtttcagg ctaaaaataa atcatgcaat gaataaaaaa gttagatacg acactgtaga   180
gggattcgct gatacagtct gtccgaacgc gtggtacc                           218

<210> SEQ ID NO 10
<211> LENGTH: 182
<212> TYPE: DNA
<213> ORGANISM: Artificial Sequence
<220> FEATURE:
<223> OTHER INFORMATION: Regulon and restriction site

<400> SEQUENCE: 10
ggtaccggcg cgccccagct ctctgcagcc caggaacaat aaatacttcc tccccatgtt    60
taaaaataac cccatgaccg cttttggcag tcataggtga ggcgggcacc acctaaggcc   120
cccccacccc atgccgttct tctgaagtaa gggtggctca ctcgccactg acgcgtggta   180
cc                                                                  182

<210> SEQ ID NO 11
<211> LENGTH: 116
<212> TYPE: DNA
<213> ORGANISM: Artificial Sequence
<220> FEATURE:
<223> OTHER INFORMATION: Regulon and restriction site

<400> SEQUENCE: 11
ggtaccggcg cgccattatt cttttttttac aaagcgtttt ctttccttat tatttatttt    60
tgcttgggct aattttaaaa tgagttttta ttcccttggt acaaacgcgt ggtacc        116

<210> SEQ ID NO 12
<211> LENGTH: 298
<212> TYPE: DNA
<213> ORGANISM: Artificial Sequence
<220> FEATURE:
<223> OTHER INFORMATION: Regulon and restriction site

<400> SEQUENCE: 12
ggtaccggcg cgcctgaatc aggaagaaat gtgagagggc cattcctttg gtggtgatca    60
catcgctcag caatgcaagt catcctattt gtcaagagtc aggggacagc tgtctgttga   120
cattgcacca catcactgcc ctttttttct ttgtcagctt tcatatgact acctatcaag   180
aaaatgtaga tgccctacat atcacacccc cagtaatatc tttctgataa gcagacttat   240
caacacttca cttagggggaa acttgtccca ggacatccta ttccctacgc gtggtacc    298

<210> SEQ ID NO 13
<211> LENGTH: 276
<212> TYPE: DNA
<213> ORGANISM: Artificial Sequence
<220> FEATURE:
<223> OTHER INFORMATION: Regulon and restriction site

<400> SEQUENCE: 13
ggtaccggcg cgccgattgt catagtaacg ctctgaaaag attttgatgc aactttggaa    60
ttacttcaca cccaattaca tagaacatct acttggaatg agataagt gcttctgtga    120 ctgcaaacat agatagaaaa tccattaacc ttttttagcca tttattaaag cagaggaaaa   180
```

```
ttattttttaa aatgcaattt ctgacttcaa gaagaagtac cgaaaaaaat attttcttgg    240
tgtagtttgg agtttcctaa taaaacgcgt ggtacc                              276

<210> SEQ ID NO 14
<211> LENGTH: 396
<212> TYPE: DNA
<213> ORGANISM: Artificial Sequence
<220> FEATURE:
<223> OTHER INFORMATION: Regulon and restriction site

<400> SEQUENCE: 14
ggtaccggcg cgccaagatg atgtccttcc ttatttggtg gctctggaag ccacattccc    60
tcctcatccg ccttcccaaa agaaccttgt ggctgcccag cggaagccag tgctttcagc    120
agcccccacc cttggcattt ccttatctag gagtcttcac tgtggaattc caaggcccac    180
cccaatgctc cggatgtgtt tcaatccatg gcctgccact ttgttactct tgtgatgaca    240
agcagataac atagctcaca tgccttcttt tcctgcatac caaccagacc ccagttctga    300
aaaggaaaca aaccacaaac caagagagat gtgttatttt tatgcagaca ttgttaagac    360
actgcaataa gcctagaatt gtggacgcgt ggtacc                              396

<210> SEQ ID NO 15
<211> LENGTH: 688
<212> TYPE: DNA
<213> ORGANISM: Artificial Sequence
<220> FEATURE:
<223> OTHER INFORMATION: Regulon and restriction site

<400> SEQUENCE: 15
ggtaccggcg cgcctccagt caggcccgcc tgagattacc taggtgttct ggtgacttct    60
gagggcctcg catgaaagat aacgcccaaa tcaacaaatc tgccattgtg gctttgaaga    120
gactgtttca atcactttat tttgtcttta tgtcaggttt gccagatggc ttgggtcttt    180
ctgaggtcct gtaccgaggg ggcacagaga gaactggtgc agcttcaaag ctcctttttta    240 atctttagca acatcacagc ggctgggaaa ctgcctcggc tccctcaagt ctctcccaca    300
aaagaggcgc ggccgaggct ctaatgaaag ccagataaag ggatggctgg aatcagaaac    360
agagggaaaa gagcagtcgt tagtctttct tgtagctgtt tcaaaagaaa ttctaagaca    420
aattatggct ttgggtgttt ttctaaaagg actgcagcag ggagaggagg tgggggaggt    480
gctttgaccc ctcagcaccc ttcccttgc atgaaaggca gaggagactg aaaaaaggct    540
gaaatacaac aataaacttt ctgcttgtgc gcgtggggat gaaaggcgcg ctggcataat    600
tatgggcgag ggtgcgcggg ggcgggcggg cggctttacc ttgccgccag cgctattaat    660
gatgaggctc cctcttacgc gtggtacc                                       688

<210> SEQ ID NO 16
<211> LENGTH: 149
<212> TYPE: DNA
<213> ORGANISM: Artificial Sequence
<220> FEATURE:
<223> OTHER INFORMATION: Regulon and restriction site

<400> SEQUENCE: 16
ggtaccggcg cgccacctca tgaccccagc cccacccctg cagtgcacaa tagggacagg    60
gccataaaag gatatggcta ggcttagggg ctattttggg gcctggggag ggcattgttc    120
aggctcagga atgggtaacg cgtggtacc                                      149
```

```
<210> SEQ ID NO 17
<211> LENGTH: 371
<212> TYPE: DNA
<213> ORGANISM: Mus musculus

<400> SEQUENCE: 17 ggtgacccctt acccagttgt tcaactcacc cttcagatta aaataactg aggtaagggc       60 ctgggtaggg gaggtggtgt gagacgctcc tgtctctcct ctatctgccc atcggccctt     120
tggggaggag gaatgtgccc aaggactaaa aaaaggccat ggagccagag gggcgagggc     180
aacagacctt tcatgggcaa accttggggc cctgctgtcc tcctgtcacc tccagagcca     240
agggatcaaa ggaggaggag ccaggacagg agggaagtgg gagggagggt cccagcagag     300
gactccaaat ttaggcagca ggcatatggg atgggatata aaggggctgg agcactgaga     360
gctgtcagag a                                                          371

<210> SEQ ID NO 18
<211> LENGTH: 371
<212> TYPE: DNA
<213> ORGANISM: Rattus norvegicus

<400> SEQUENCE: 18
acccttaccc agtgtgttca actcagcctt tcagattaaa aataactaag gtaagggcca       60
tgtgggtagg ggaggtggtg tgagacggtc ctgtctctcc tctatctgcc catcggccct     120
ttggggagga ggaaatgtgc ccaaggacta aaaaaggcct ggagccagag gggctagggc     180
taagcagacc tttcatgggc aaacctcagg gctgctgtcc tcctgtcacc tccagagcca     240
agggatcaaa ggaggaggag ccagacagga gggatgggag ggagggtccc agcagatgac     300
tccaaattta ggcagcaggc acgtggaatg agctataaag gggctggagc gctgagagct     360
gtcagaccga g                                                          371

<210> SEQ ID NO 19
<211> LENGTH: 371
<212> TYPE: DNA
<213> ORGANISM: Homo sapiens

<400> SEQUENCE: 19
gtgaccctca cccatgtttt cagtctcact tcgggggaaa ataactgag gtaagggcca       60 tggcagggtg ggagaggcgg tgtgagaagg tccagtcttc ccagctatct gctcatcagc     120
cctttgaagg ggaggaatgt gcccaaggac taaaaaaagg ccgtggagcc agagaggctg     180
gggcagcaga cctttcaagg gcaaatcagg ggccctgctg tcctcctgtc acctccagag     240
ccaaaggatc aaaggaggag gagccaggag gggagagagg tgggagggag ggttcctgtc     300
acctccagag cctccggaag gactccaaat ttagacagag ggtgggggaa acgggatata     360
aaggaactgg a                                                          371

<210> SEQ ID NO 20
<211> LENGTH: 44
<212> TYPE: DNA
<213> ORGANISM: Artificial Sequence
<220> FEATURE:
<223> OTHER INFORMATION: Primer

<400> SEQUENCE: 20
ataggtaccg gtgacccctta cccagttgtt caactcaccc ttca                      44
```

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
atagctagcg ggttggagaa atctctgaca gct                        33

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
ttgctagcac catggtgagc aagcagatcc tgaagaacac                 40

<210> SEQ ID NO 23
<211> LENGTH: 36
<212> TYPE: DNA
<213> ORGANISM: Artificial Sequence
<220> FEATURE:
<223> OTHER INFORMATION: Primer

<400> SEQUENCE: 23
ttaagatctt tacacccact cgtgcaggct gcccag                     36

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
atatctagaa tcccggccgg gaacg                                 25

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
atagctagca atcgatgttc gaatcccaat tctttg                     36

<210> SEQ ID NO 26
<211> LENGTH: 17
<212> TYPE: DNA
<213> ORGANISM: Artificial Sequence
<220> FEATURE:
<223> OTHER INFORMATION: Primer

<400> SEQUENCE: 26
gccttctagc cagccat                                          17

<210> SEQ ID NO 27
<211> LENGTH: 19
<212> TYPE: DNA
<213> ORGANISM: Artificial Sequence
<220> FEATURE:
<223> OTHER INFORMATION: Primer

```
<400> SEQUENCE: 27
ggcaccttcc agggtcaag                                                   19

<210> SEQ ID NO 28
<211> LENGTH: 20
<212> TYPE: DNA
<213> ORGANISM: Artificial Sequence
<220> FEATURE:
<223> OTHER INFORMATION: Probe

<400> SEQUENCE: 28
tgtttgcccc tcccccgtgc                                                  20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tgtgtccgtc gtggatctga                                                  20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
cctgcttcac caccttcttg a                                                21
```